(12) United States Patent
Dai et al.

(10) Patent No.: US 9,880,116 B2
(45) Date of Patent: Jan. 30, 2018

(54) HIGH-THROUGHPUT SORTING OF SMALL OBJECTS VIA OIL AND/OR MOISTURE CONTENT USING LOW-FIELD NUCLEAR MAGNETIC RESONANCE

(71) Applicant: Monsanto Technology LLC, St. Louis, MO (US)

(72) Inventors: Bin Dai, St. Louis, MO (US); Susan Macisaac, St. Louis, MO (US); Kevin L. Deppermann, St. Louis, MO (US); Mark Ehrhardt, St. Louis, MO (US); Brad White, St. Louis, MO (US); Wayne Brown, St. Louis, MO (US); Paul Krasucki, St. Louis, MO (US); Jemmi C. McDonald, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/371,871

(22) Filed: Dec. 7, 2016

(65) Prior Publication Data

US 2017/0089849 A1   Mar. 30, 2017

Related U.S. Application Data

(63) Continuation of application No. 14/206,238, filed on Mar. 12, 2014, now Pat. No. 9,658,176.
(Continued)

(51) Int. Cl.
*A01C 1/00* (2006.01)
*G01R 33/30* (2006.01)
(Continued)

(52) U.S. Cl.
CPC ............... *G01N 24/08* (2013.01); *A01C 1/00* (2013.01); *G01R 33/307* (2013.01); *G01R 33/445* (2013.01); *G01R 33/561* (2013.01)

(58) Field of Classification Search
CPC ........ G01N 24/08; A01C 1/00; G01R 33/561; G01R 33/445; G01R 33/307
See application file for complete search history.

(56) References Cited

U.S. PATENT DOCUMENTS

2002/0144458 A1 * 10/2002 Hunter .................... A01C 1/00
47/14
2006/0042528 A1    3/2006 Deppermann
(Continued)

FOREIGN PATENT DOCUMENTS

| CN | 101772300 A | 7/2010 |
| CN | 101929961 A | 12/2010 |

(Continued)

OTHER PUBLICATIONS

PCT International Report on Patentability, PCT US2014/025174, dated Sep. 15, 2015.
(Continued)

*Primary Examiner* — G. M. Hyder
(74) *Attorney, Agent, or Firm* — Polster Lieder

(57) ABSTRACT

The current disclosure describes an automated high-throughput seed sorting system for separating seed via oil and/or moisture content using novel nuclear magnetic resonance (NMR) systems and methods. The disclosed systems and methods for measuring the oil and/or moisture content of a single seed in a low-field time domain NMR instrument are superior in sample throughput and signal-to-noise ratio to conventional NMR systems and methods (free induction decay or spin echo) for single seed oil/moisture measurement.

11 Claims, 21 Drawing Sheets

Related U.S. Application Data

(60) Provisional application No. 61/791,411, filed on Mar. 15, 2013.

(51) Int. Cl.
*G01N 24/08* (2006.01)
*G01R 33/44* (2006.01)
*G01R 33/561* (2006.01)

(56) References Cited

U.S. PATENT DOCUMENTS

| | | |
|---|---|---|
| 2010/0176818 A1 | 7/2010 | Herrmann et al. |
| 2010/0308822 A1 | 12/2010 | Prado et al. |
| 2012/0228199 A1 | 9/2012 | Modiano et al. |

FOREIGN PATENT DOCUMENTS

| | | |
|---|---|---|
| CN | 202146867 U | 2/2012 |
| WO | 2012028785 A1 | 8/2012 |

OTHER PUBLICATIONS

PCT Search Report, PCT US2014/025174, dated Jul. 3, 2014.
Chinese Office Action, Patent Application No. 201480016137.4, dated Nov. 17, 2016.

\* cited by examiner

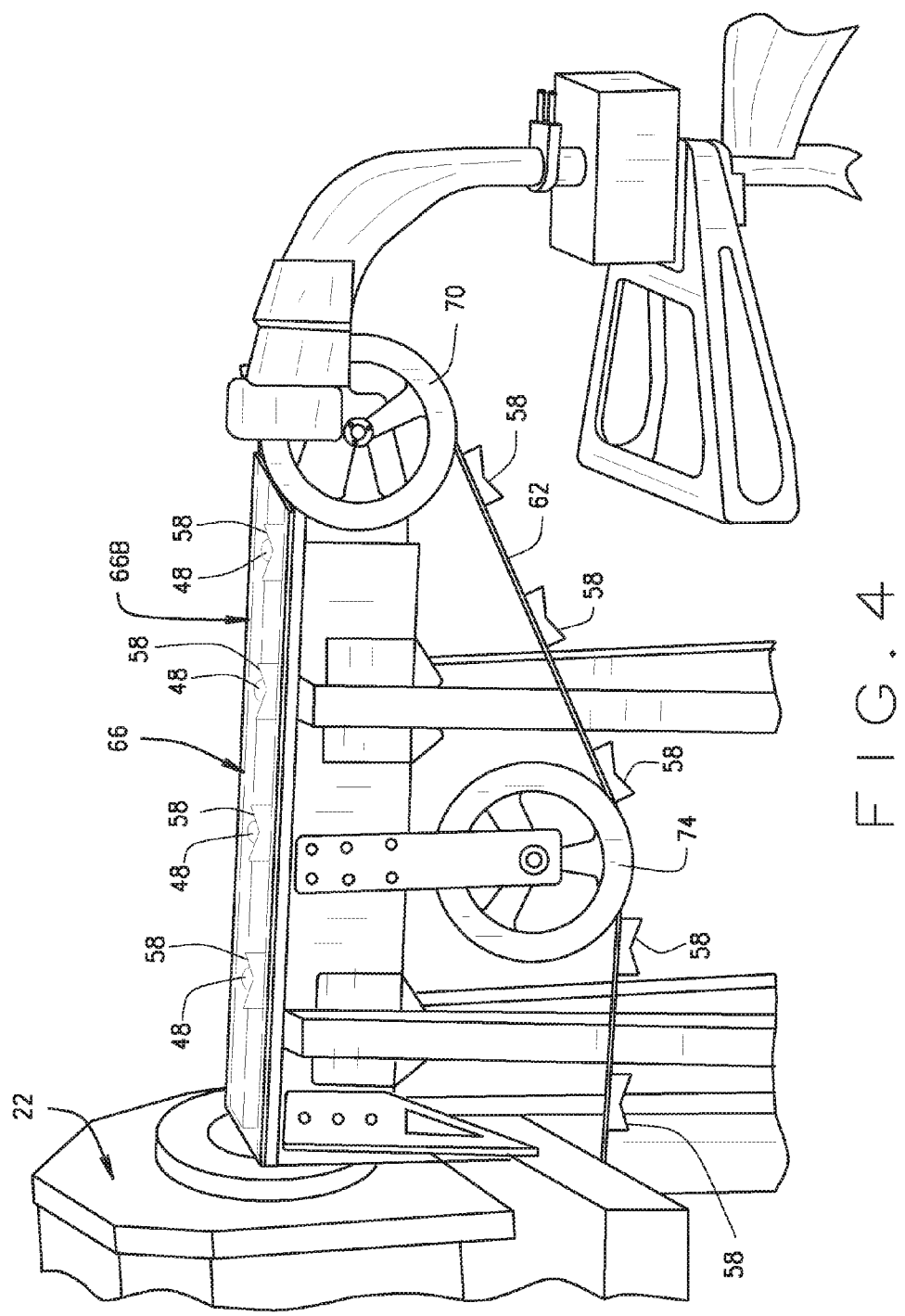

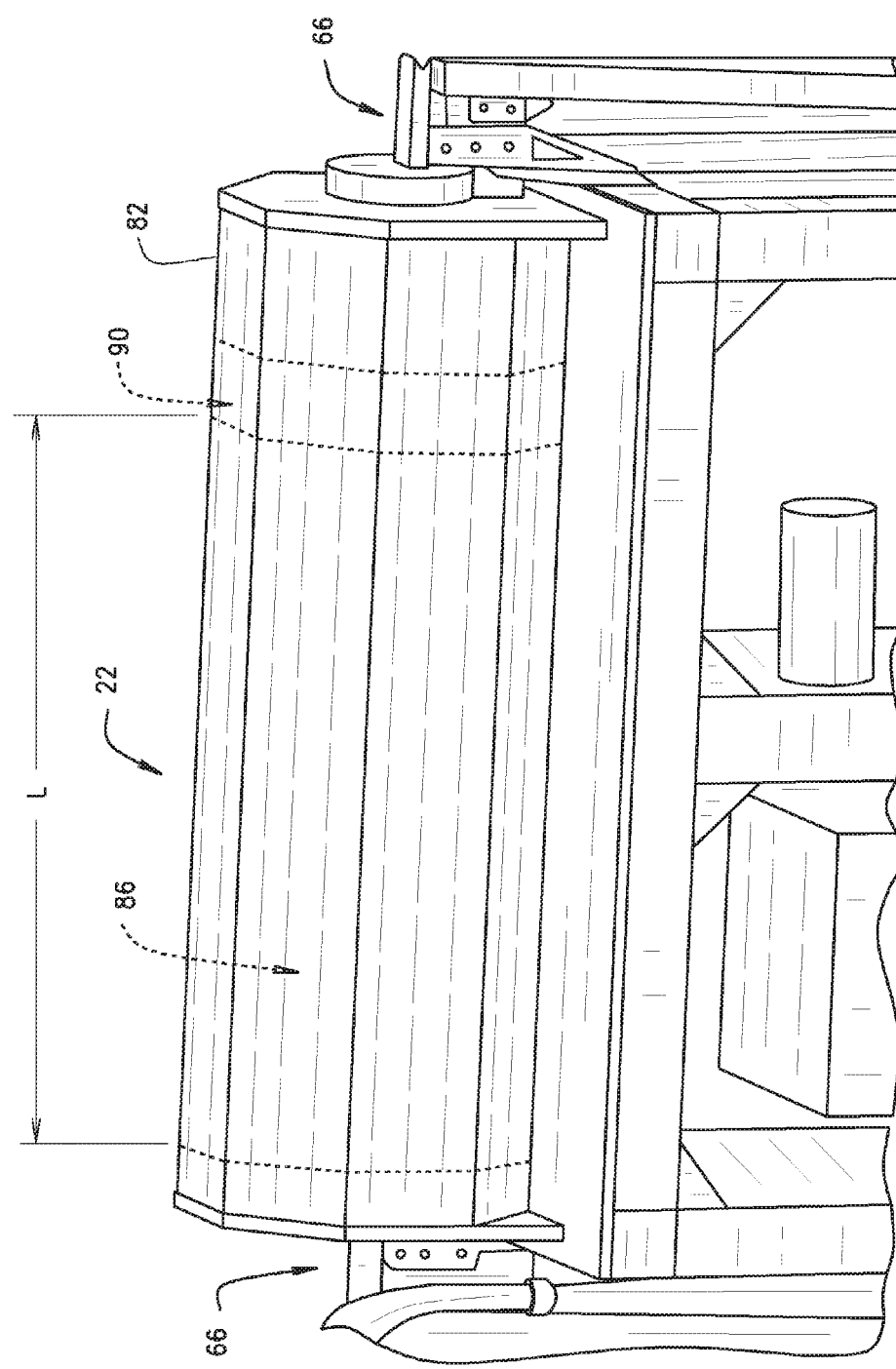

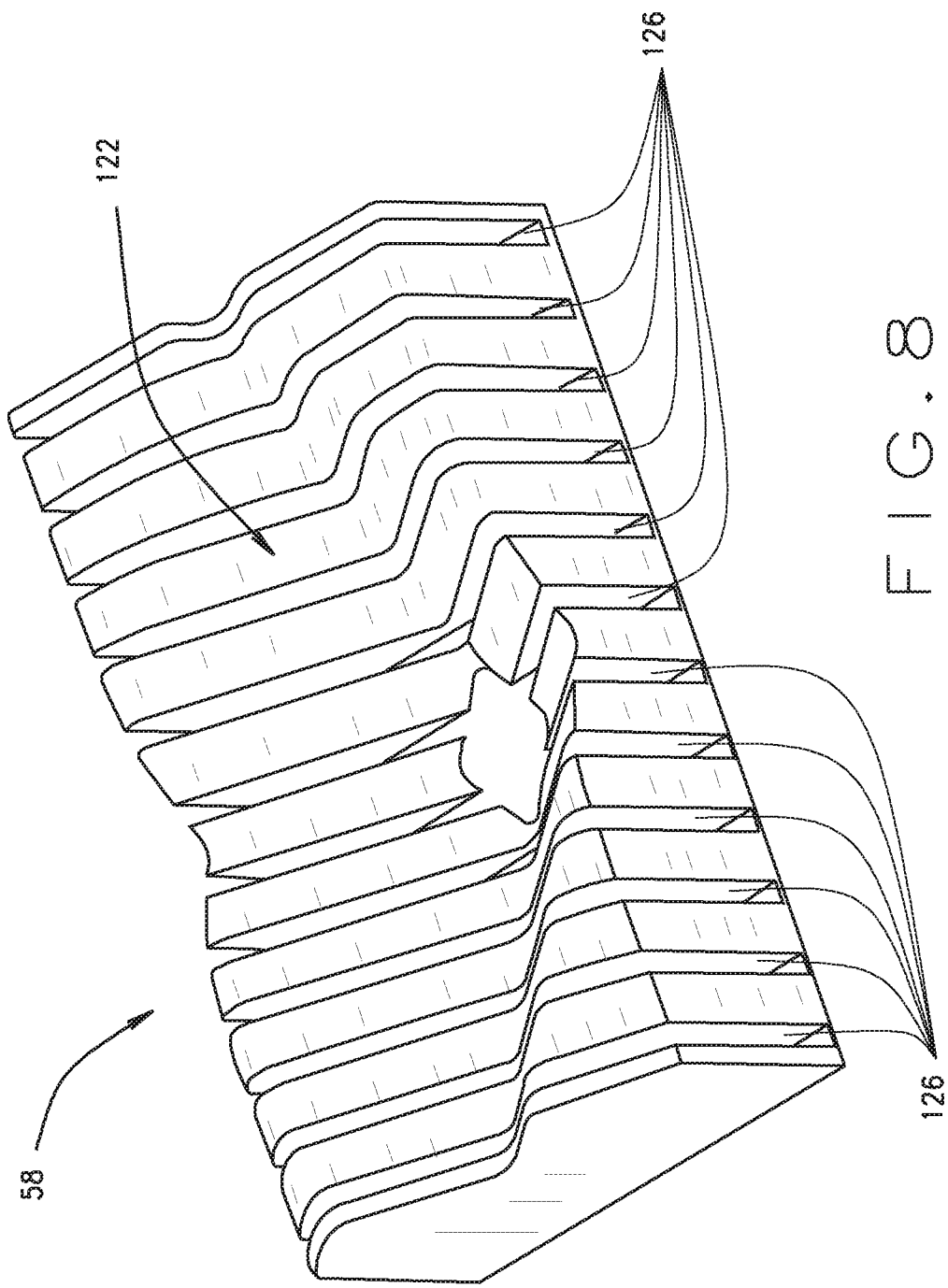

HIGH-THROUGHPUT SORTING OF SMALL OBJECTS VIA OIL AND/OR MOISTURE CONTENT USING LOW-FIELD NUCLEAR MAGNETIC RESONANCE

CROSS-REFERENCE TO RELATED APPLICATIONS

This application is a continuation of U.S. patent application Ser. No. 14/206,238 filed on Mar. 12, 2014, which claims the benefit of U.S. Provisional Application No. 61/791,411, filed on Mar. 15, 2013, the disclosure of which are incorporated herein by reference in their entirety.

FIELD

The present disclosure relates generally to low-field time domain NMR systems and methods for measuring oil and/or moisture content of small object samples (e.g., seed samples). More particularly, it relates to automated systems and methods for using NMR relaxometry for the high-throughput continuous sorting of small objects (e.g., seeds) via measuring the oil and/or moisture content dynamically.

BACKGROUND

The statements in this section merely provide background information related to the present disclosure and may not constitute prior art.

Low-field NMR relaxometry has been increasingly used in many analytical applications, for example, determining oil and/or moisture content in small objects, such as seeds, measuring xylene solubility in polyethylene, and determining the solid to liquid fat ratio in margarine. Conventional NMR methods for determining the oil/moisture content in small object samples using the Hahn spin-echo pulse technique has become an international standard method (AOCS, American Oil Chemist Society, official method, 1995). Despite its wide use in analytical laboratories for nondestructive oil measurement, the Hahn spin echo, and other known NMR based methods requires an undesirably long time for an individual measurement.

SUMMARY

The current disclosure describes automated high-throughput small object sorting systems and methods for separating small objects (e.g., seeds) via oil and/or moisture content using a nuclear magnetic resonance (NMR) method. The NMR systems and methods described herein are superior to conventional NMR methods (e.g., free induction decay or spin echo) for nondestructive single object oil and/or moisture measurement in terms of sample throughput and signal-to-noise ratio. This nondestructive analytical technique has the potential of evaluating the oil and/or moisture content in 30,000 to 50,000 individual small objects, or more, per hour using a low-field NMR relaxometer. The continuous high-throughput NMR-based systems and methods described herein provide the ability to rapidly and accurately measure the oil and/or moisture content in a moving small object.

For example, in various embodiments, the present disclosure provides an automated high-throughput small object sorting system including a small object conveyor belt having a plurality of small object cups attached thereto, wherein the conveyor assembly is structured and operable to continuously move the conveyor belt at a selected constant rate of speed during operation of the system. The system additionally includes a small object feeder assembly that is structured and operable to singulate small objects from a plurality of small objects and deposit each singulated small object into a respective one of the small object cups as the conveyor belt continuously moves at the selected constant rate of speed. The system further includes a nuclear magnetic resonance (NMR) assembly having the conveyor belt operably extending therethrough. The NMR assembly is structured and operable to generate oil and/or moisture mass data for each small object as each small object moves through the NMR assembly at the selected constant rate of speed.

Still further, the system includes a microwave resonance cavity that is structured and operable to receive and have pass therethrough, without pause, each small object after each respective small object has been conveyed through the NMR assembly, and to obtain total small object mass data for each respective small object. Further yet, the system includes a computer based central control system that is structured and operable to: receive the at least one of oil and moisture mass data from the NMR assembly for each small object; receive the total small object mass from the microwave resonance cavity for each small object; and execute oil/moisture content software. Execution of the oil/moisture content software will store oil and/or moisture mass data for each small object and associate the at least one of oil and moisture mass data received for each small object with the respective small object. Execution of the oil/moisture content software will additionally store the total small object mass data for each small object and associate the total small object mass data for each small object with the respective small object. Furthermore, execution of the oil/moisture content software will compute, based on the at least one of oil and moisture mass and total mass data for each small object, an oil/moisture content value for each respective small object within a time period dictated by the selected constant rate of speed of the conveyor belt.

Although the systems and methods described herein can be used to measure the oil and/or moisture content of various small objects, the present disclosure will exemplarily describe the inventive systems and methods with regard to seeds. However, such exemplary embodiments and description should not be considered as limiting the scope of the present disclosure.

For example, continuous high-throughput NMR-based systems and methods described herein are particularly useful for separating haploid from diploid seeds generated with a high oil inducer, a key step in the double haploid breeding process. Separation of haploid from diploid seeds can be achieved based on oil content differences. A method of measuring the oil content of a single seed in a low-field time domain NMR instrument is described in detail below.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 4 is an isometric view of a distal end of the small object conveyor assembly of the high throughput dynamic small object sorting system shown in FIG. 1, in accordance with various embodiments of the present disclosure.

FIG. 5 is a side view of a nuclear magnetic resonance assembly of the high throughput dynamic small object sorting system shown in FIG. 1, in accordance with various embodiments of the present disclosure.

FIG. 8 is an isometric view of one of a plurality of small object cups of the high throughput dynamic small object sorting system shown in FIG. 1, in accordance with various embodiments of the present disclosure.

Corresponding reference numerals indicate corresponding parts throughout the several views of drawings.

DETAILED DESCRIPTION

Figure 1:
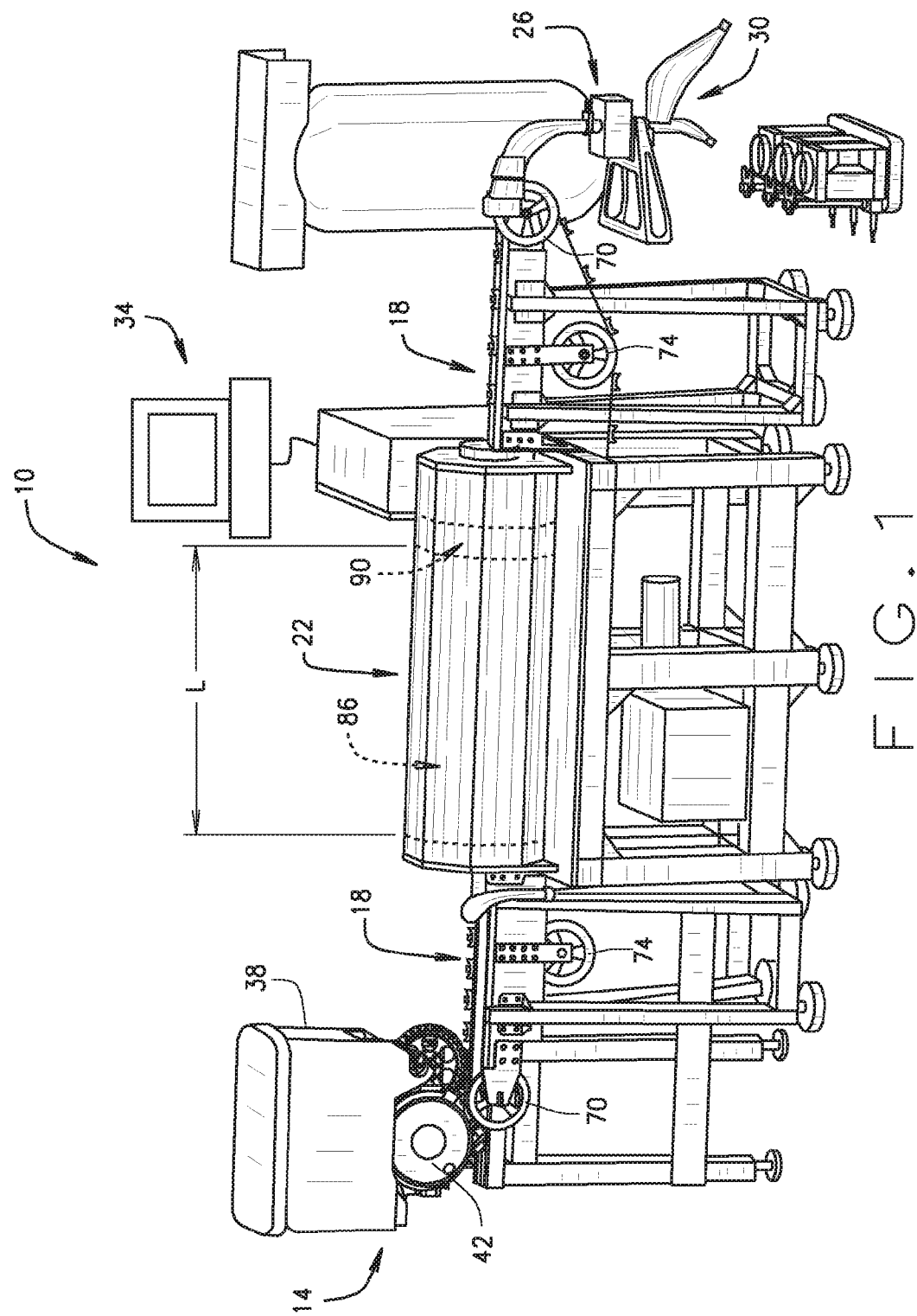
FIG. 1 is an isometric view of a high throughput dynamic small object sorting system that utilizes nuclear magnetic resonance to sort small objects based on oil and/or moisture content, in accordance with various embodiments of the present disclosure.
Figure 2:
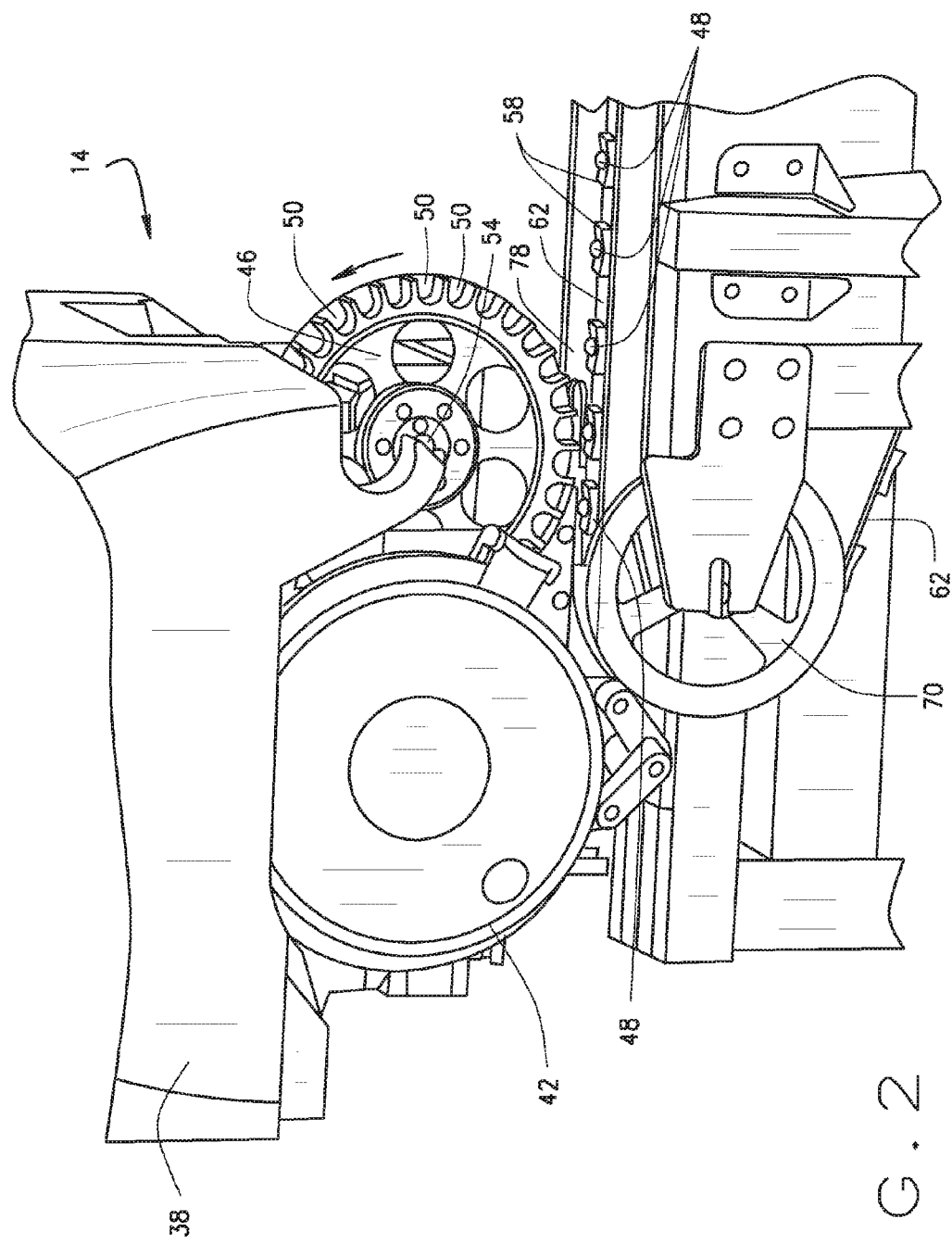
FIG. 2 is an isometric view of a small object feeder assembly of the high throughput dynamic small object sorting system shown in FIG. 1, in accordance with various embodiments of the present disclosure.

The following description is merely exemplary in nature and is in no way intended to limit the present teachings, application, or uses. Throughout this specification, like reference numerals will be used to refer to like elements.

Described herein are systems and methods for the ultra-fast determination of the oil and/or moisture content of a single small object (e.g., a single seed). Generally, the systems and methods described herein employ a train of 90° pulse sequences, or alternatively a combination of a single 90° pulse and a train of 180° pulses, to produce an NMR signal in a low-field NMR relaxometer. The amplitude of the NMR signal obtained is directly proportional to the oil and/or moisture content of the object. Due to the significant improvement of signal-to-noise ratio (S/N), the disclosed NMR systems and methods can accurately determine the oil and/or moisture content of a single small object sample (e.g., a single seed sample) within an extremely short time period, e.g., within 5 to 30 milliseconds, which enables the high-throughput sorting of objects based on their oil and/or moisture content difference. Additionally, the disclosed systems and methods allow object samples to be measured in a continuous and dynamic fashion, thereby making automatic high-speed sorting by NMR possible.

Referring now to FIG. 1, the present disclosure provides a high throughput dynamic small object sorting system 10 that utilizes nuclear magnetic resonance to sort small objects based on oil and/or moisture content. Generally, the system 10 includes a feeder assembly 14, a conveyor assembly 18, a nuclear magnetic resonance (NMR) assembly 22, a microwave resonance cavity 26, a diverter assembly 30, and a computer based central control system 34. The control system 34 is structured and operable to directly or indirectly control and coordinate the automated and cooperative functions and operations of the feeder assembly 14, the conveyor assembly 18, NMR assembly 22, the microwave resonance cavity 26, and the diverter assembly 30, as described below. The control system 34 is further structured and operable to execute one or more oil and/or moisture content analysis programs or algorithms (simply referred to herein as oil/moisture content analysis software) for analyzing data generated and collected by the system 10 to identify and separate small objects (e.g., separate haploid seeds from diploid seeds) based on oil and/or moisture content, at a high rate of speed, e.g., 5 to 30 milliseconds/seed, as also described further below.

More specifically, the system 10, as controlled by the central control system 34, is structured and operable to singulate small objects (e.g., seeds) from a plurality of small objects (e.g., seeds) via the feeder assembly 14, dynamically transport the singulated small objects through the NMR assembly 22 at a high rate of speed via the conveyor assembly 18, collect oil and/or moisture mass data for each individual object as the objects are dynamically transported through the NMR assembly 22, collect total object mass data for each individual object via the microwave resonance cavity 26, calculate the oil and/or moisture content for each individual small object, and separate the small objects (e.g., separate haploid seeds from diploid seeds) based on the respective oil and/or moisture content via the diverter assembly 30, at a high rate of speed, e.g., 20 to 50 seeds per second.

It should be understood that although the system 10, as described herein, can be used to measure the oil and/or moisture content of various small objects, for simplicity and clarity the present disclosure will exemplarily describe the system 10 for use in measuring the oil content of seeds. However, such exemplary embodiments and description should not be considered as limiting the scope of the present disclosure.

Additionally, it is envisioned that the system 10 described herein can include additional and/or alternative sensing and detection technologies to measure characteristics of the small objects (e.g., seeds) other than moisture and/or oil content, such that the small objects (e.g., seeds) can be sorted based on moisture content and/or oil content and/or some other identifiable and distinguishable characteristic(s) of the small objects (e.g., seeds), and remain within the scope of the present disclosure.

Referring now to FIGS. 1, 2, 3A and 3B, in various embodiments, the feeder assembly 14 (hereafter the seed feeder assembly 14) comprises a bulk seed hopper 38, a seed singulator 42, and a rotating seed dispensing sprocket 46. The bulk seed hopper 38 is structured and operable to retain a desired quantity of selected seeds and to feed the seeds into the singulator 42. The singulator 42 is structured and operable to singulate individual seeds 48 from the hopper 38, i.e., parse, or separate, the seeds 48 one-by-one from the plurality of seeds in the hopper 38. The singulator 42 is further structured and operable to place each singulated seed 48 into a respective one of a plurality of seed reservoirs 50 formed in the periphery of the dispensing sprocket 46. More particularly, during operation of the seed feeder assembly 14, the dispensing sprocket 46 is rotated about a dispensing sprocket axle 54. As the dispensing sprocket 46 rotates, the singulator 42 deposits each singulated seed 48, i.e., parsed seed 48, into a respective one of the seed reservoirs 50. Subsequently, as the dispensing sprocket 46 continues to rotate, each seed 48 that has been deposited into one the seed reservoirs 50 is deposited into a respective one of a plurality of seed cups 58 that are connected to a conveyor belt 62 of the seed conveyor assembly 18, as described further below.

Referring now to FIGS. 1, 2, 3A, 3B, 4 and 8, in various embodiments the seed conveyor assembly 18 includes the seed cups 58 connected to the conveyor belt 62 that is slidingly disposed within a conveyor track 66, and at least one drive wheel 70 operably connected to at least one drive motor (not shown) to drive the conveyor belt 62 along the track 66, i.e., cause the conveyor belt 62 and seed cups 58 to travel along the track 66. More specifically, the drive motor(s) are structured and operable, as controlled by the central control system 34, to drive the conveyor belt 62 at a constant rate of speed, e.g., 0.5 to 2 meters per second, such that the seed cups 58, and more importantly the singulated seeds 48 disposed in the seed cups 58, are conveyed, or transported, from a proximal end 66A of the conveyor track 66, through the NMR assembly 22, to a distal end 66B of the convey track at a constant rate of speed. For example, in various embodiments, the drive motor(s) are controlled by the central control system 34 to drive the conveyor belt 62 at a selected rate of speed such that each seed 48 is deposited into the respective seed cup 58 at the conveyor belt track proximal end 66A and conveyed through the NMR assembly 22 to the conveyor belt track distal end 66B of the conveyor track 66 within approximately 1 second, or alternatively approximately 0.5 to 1.5 seconds. In various implementations, the conveyor assembly 18 additionally includes at least one passive belt guide wheel 74 to guide the conveyor belt 62 as it travels beneath the conveyor belt track 66 and a track cover 78 that covers the conveyor belt track 66 and prevents seeds 48 from being dislocated from the respective seed cups 58.

Referring now to FIG. 5, in various embodiments, the NMR assembly 22 comprises a housing 82 that encloses a nuclear magnetic resonance (NMR) relaxometer 86, i.e., a nuclear magnet, and a radio frequency (RF) probe 90, i.e. a RF transceiver. In various embodiments, the NMR relaxometer 86 has a longitudinal length L of approximately 0.50 to 1.5 meters, e.g., approximately 0.78 meters, and the relaxometer plus the RF probe have an overall length of between 0.75 and 2.0 meters, e.g., 1.1 meters. As described above, the conveyor belt 62 conveys the seeds 48 through the NMR assembly 22 at a selected constant rate of speed, e.g., 1.0-1.5 meters/second. More particularly, the conveyor belt 62, as controlled by the central control system 34, conveys the seeds 48 past, or through, the entire length of NMR relaxometer 86 and past, or through, the RF probe 90 at the selected constant rate of speed. During operation of the system 10, as the seeds 48 are conveyed past/through the NMR relaxometer 86, at the selected constant rate of speed, a magnetic field generated by the NMR relaxometer 85 is exerted on the seeds 48. The magnetic field causes the protons of each respective seed 48 to align parallel to the direction of the magnetic field.

Importantly, and as described further below in Experiment No. 2, the seeds 48 are moving at a constant rate of speed via the conveyor belt 62 and only pass through the NMR assembly 22 once. That is, the seeds 48 are never static as is the case with a traditional NMR pulse sequence that scans a static sample multiple times. Moreover, given the extended length L of the NMR relaxometer 86, e.g., 0.5-1.5 meters, and the constant rate of speed of conveyance of each seed 48 through the NMR relaxometer, e.g., 1.0-1.5 meters/second, each seed 48 is exposed to the NMR magnetic field, i.e., each seed 48 is polarized, for an extended period of time, e.g., 0.5-3.0 seconds. Accordingly, each constantly moving seed 48 is exposed to the NMR magnetic field for a sufficient time for the protons of each respective seed 48 to align parallel to the direction of the magnetic field without slowing or stopping the rate of speed of conveyance of each seed 48.

Subsequently, as the seeds 48 continue to move through and along the length of the NMR relaxometer 86 and pass through the RF probe 90 at the selected constant rate of speed, the RF probe 90 generates one or more pulses and receives an echo from each pulse. For example, the RF probe 90 can generate a plurality of pulses at any desired interval, e.g., 5 pulses/millisecond, or approximately 100-200 microseconds between pulses, and receive an echo from each pulse. Each pulse disrupts, or disturbs, the proton alignment, whereby the amount of proton disruption is identified in the echo received from each pulse. The central control system 34, via execution of the oil content analysis software, utilizes the amount of proton disruption from each echo to generate data indicative of the mass of oil in each respective seed, hereafter referred to oil mass data.

Note, that as described above, it is envisioned that the system 10 can be used to measure oil content and/or moisture content (and/or other distinguishable characteristics) in various small objects other than seeds. Hence, in such alternate embodiments, the central control system 34 would execute oil and/or moisture content analysis software, to utilize the amount of proton disruption from each echo to generate data indicative of the mass of oil and/or moisture in each respective small object.

Continuing now with the exemplary seed embodiment, subsequently, via execution of the oil content analysis software, the central control system 34 records and saves the oil mass data, i.e., the oil mass data from each pulse echo and associates, links or ties the oil mass data to the respective seed 48. Hence, seeds 48 are constantly moving at the selected constant rate of speed, e.g., 1 m/sec, (that is, in a dynamic state as opposed to a static state) as the protons are aligned, via the NMR relaxometer 86, and the oil mass data is generated, via the RF probe 90, and the oil mass data is gathered and saved, via the central control system 34.

It should be noted that by generating the RF pulses and receiving the echoed oil mass data at high rate, e.g., 5 pulses/millisecond, noise in subsequent detected echoes partially cancel each other out, thereby significantly increasing the signal-to-noise ratio of the NMR signal measurement, allowing more accurate and robust measurement of oil content in the respective seeds, as described herein.

Figure 6A:
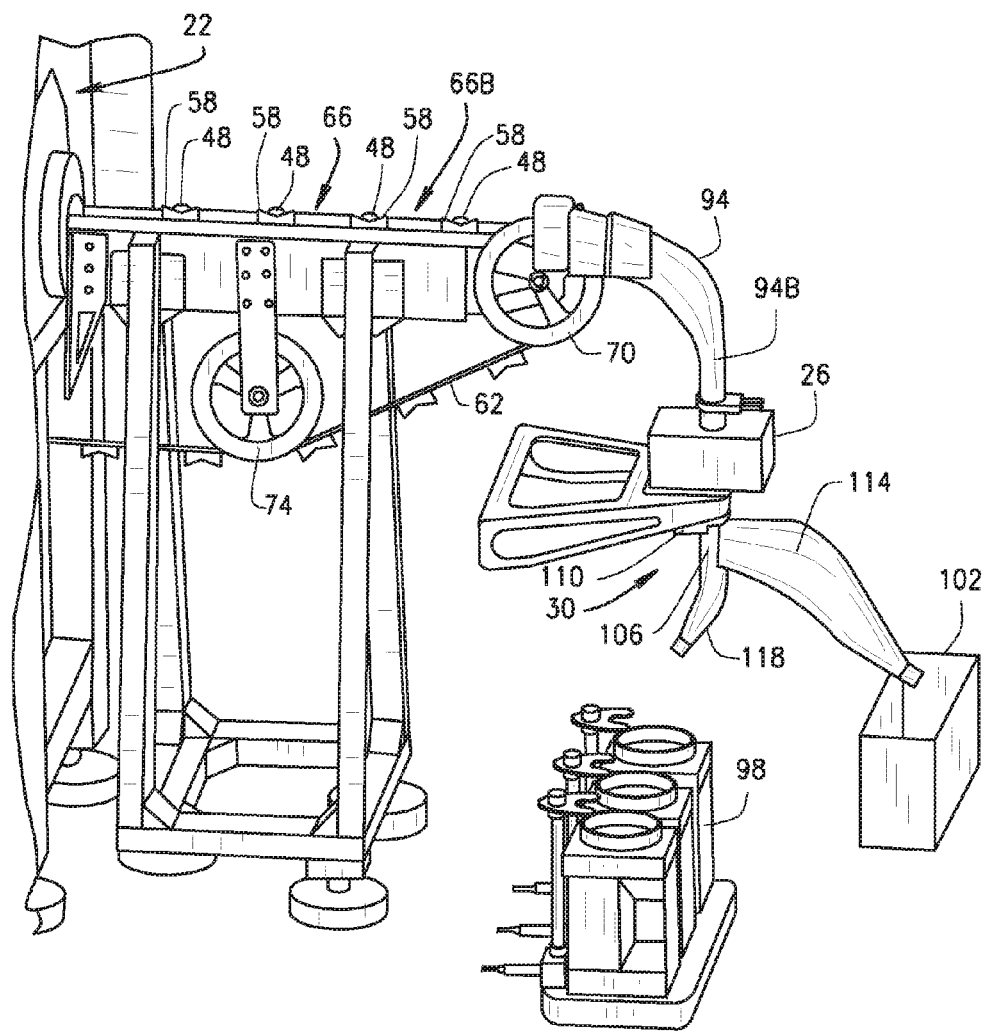
FIG. 6A is an isometric view of a microwave resonance cavity and a diverter assembly of the high throughput dynamic small object sorting system shown in FIG. 1, in accordance with various embodiments of the present disclosure.

Referring now to FIG. 6A, as described above, the system 10 includes the microwave resonance cavity 26 and the diverter assembly 30. The system 10 additionally includes an offload funnel 94 mounted to the distal end 66B of the conveyor track 66, and/or other system 10 structure located at or near the conveyor track distal end 66B. The offload funnel 94 includes an ingress end 94A and an egress end 94B. The offload funnel 94 is structured and operable to receive seeds 48 that are offloaded from the respective seed cups 58 as the conveyor belt 62 and seed cups 58 travel along the periphery of the drive wheel 70 at the distal end 66B of the convey track 66. More specifically, after each seed 48 has been conveyed through the NMR assembly 22 and the respective oil mass data has been gathered, saved and associated with the respective seed 48, as described above, each seed cup 58 and respective seed 48 is conveyed along the conveyor track distal end 66B and along the periphery of the distal end drive wheel 70. As each seed cup 58 travels along the periphery of the distal end drive wheel 70, the respective seed 48 falls out of the seed cup 58 into the offload funnel ingress end 94A.

In various embodiments, the diverter assembly 30 is connected to the microwave resonance cavity 26, wherein the egress end 94B of the offload funnel 94 is connected to the microwave resonance cavity 26. Accordingly, once each seed falls out of the respective seed cup 58 and into the offload funnel ingress end 94A, due to the force of gravity, the seeds 48 fall through the offload funnel 94 and are directed into the microwave resonance cavity 26 via the offload funnel egress end 94B. Alternatively, air can be blown through the offload funnel 94 in the direction of seed travel to assist and/or accelerate the travel speed of the seeds 48 through the offload funnel 94. In such embodiments, after the seeds 48 exit the offload funnel 94 and enter the microwave resonance cavity 26, each seed 48 falls through via gravity, or alternatively is accelerated through via forced air, an internal passage (not shown) of the microwave resonance cavity 26 and enters the diverter assembly 30.

The microwave resonance cavity 26 is structured and operable to accurately measure, or predict, the total mass of each seed 48 as it passes through the internal passage. The microwave resonance cavity 26 communicates the total mass data of each seed 48 to the central control system 34, where, via execution of the oil content analysis software, the central control system 34 records and saves the total mass data from each seed 48 and links or ties the total mass data to the respective seed 48 and the previously saved oil mass data for the respective seed 48.

Importantly, via execution of the oil content analysis software, the central control system 34 utilizes the saved oil mass data and total mass data to compute the oil content of each seed 48 as each respective seed 48 passes through the microwave resonance cavity 26. Hence, prior to each seed 48 exiting the microwave resonance cavity 26, the central control system 34 computes the oil content of the respective seed 48. Moreover, prior to each seed 48 exiting the microwave resonance cavity 26, based on the computed oil content of the respective seed 48, the central control system 34 determines whether the oil content of respective seed 48 exceeds an oil content threshold for the respective seed. That is, based on the computed oil content of the respective seed 48, the central control system 34 determines whether the oil content of respective seed 48 indicates that the seed is haploid or diploid.

Upon exiting the microwave resonance cavity 26, each seed 48 enters the diverter assembly 30 where, as controlled by the central control system 34, the diverter assembly 30 directs or diverts seeds 48 with an oil content below the respective threshold, i.e., haploid seeds, to a haploid receptacle 98 and directs or diverts seeds 48 with an oil content above the respective threshold, i.e., diploid seeds, to a diploid receptacle 102. Generally, the diverter assembly 30 includes a hollow central tube 106 that is connected at a proximal end to the microwave resonance cavity 26 (in fluid connection with the microwave resonance cavity internal passage), a diverter device 110 cooperatively connected to the central tube 106, a diverted seed funnel 114 connected to the central tube 106 (in fluid connection with an interior lumen of the central tube 26), and a non-diverted seed funnel 118 disposed at a distal end of the central tube 106 (in fluid connection with the interior lumen of the central tube 26). In operation, as each seed 48 exits the microwave resonance cavity 26 each seed 48 enters the interior lumen of the hollow central tube 106, whereafter, based on the computed oil content of each respective seed 48, each respective seed 48 is either diverted or directed into the diverted seed funnel 114, via operation of the diverter device 110 (as controlled by the central control system 34), or is allowed to fall through the central tube into the non-diverted seed funnel 118.

For example, in various embodiments, seeds 48 that are determined to be diploids, based on the computed oil content of the respective seeds 48, are diverted into the diverted seed funnel 114, whereafter the diploid seeds 48 pass through the diverted seed funnel 114 and are deposited into the diploid receptacle 102. Conversely, seeds 48 that are determined to be haploids, based on the computed oil content of the respective seeds 48, are allowed to fall through the central tube 106 into the non-diverted seed funnel 118, whereby the haploid seeds 48 are deposited into the haploid receptacle 98. In alternative embodiments, execution of the oil content analysis software could operate the diverter device 110 to divert or direct haploid seeds 48 into the diverted seed funnel 114 and allow diploid seeds 48 to fall through to the non-diverted seed funnel 118.

The diverter device 110 can be any device suitable for diverting or directing selected seeds 48 (e.g., diploid seeds) into the diverted seed funnel 114 and allow other selected seeds 48 (e.g., haploid seeds) to fall through the central tube 106 into the non-diverted seed funnel 118. For example, in various embodiments, the diverter device 110 can be a pneumatic device that controls a flow of air to divert the selected seeds 48 into the diverted seed funnel 114. Particularly, in such embodiments, if a seed 48 is determined to be a diploid while the respective seed 48 passes through the microwave resonance cavity 26, as the respective diploid seed 48 falls through the diverter device central tube 106, a valve of the pneumatic diverter device opens such that air is released that diverts or directs the respective diploid seed 48 into the diverted seed funnel 114, whereafter the respective diploid seed 48 is expelled into the diploid receptacle 102. While conversely, if a seed 48 is determined to be a haploid while the respective seed 48 passes through the microwave resonance cavity 26, as the respective diploid seed 48 falls through the diverter device central tube 106, the valve of the pneumatic diverter device remains closed such that no air is released and the respective haploid seed 48 falls through the diverted seed funnel 114 into the haploid receptacle 98. Other electro-mechanical type diverter devices 110 are envisioned and within the scope of the present disclosure.

In various embodiments, it is envisioned that the oil/moisture content analysis software and the diverter assembly 30 can be structured and operable to divert seeds (or small objects) to more than two different receptacles.

Figure 6B:
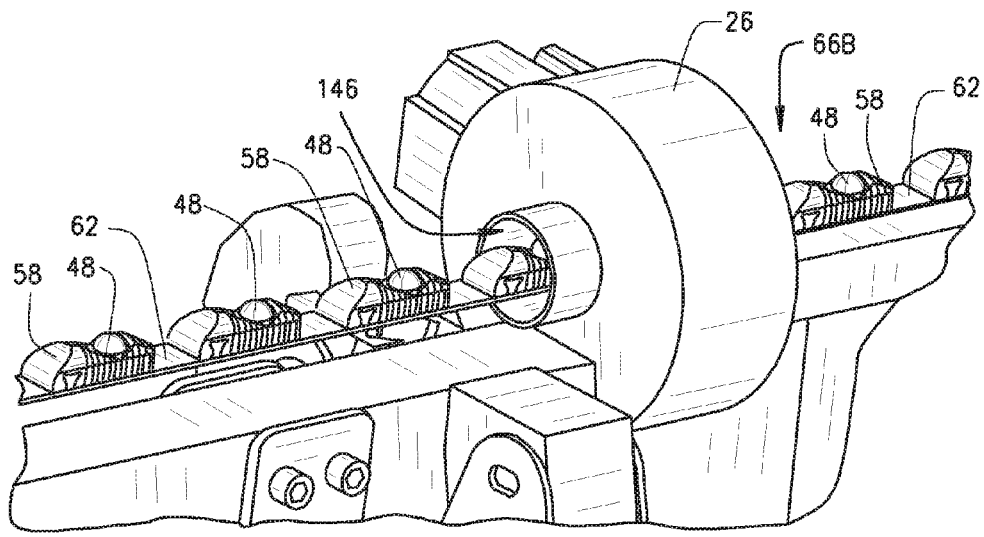
FIG. 6B is an isometric view of an inline microwave resonance cavity, in accordance with various other embodiments of the present disclosure.

Referring now to FIG. 6B, in various embodiments, the microwave resonance cavity 26 can be an inline microwave resonance cavity 26' disposed near the distal end 66B of the conveyor belt 66. In various implementations, the inline microwave resonance cavity 26' can be structured to such that the conveyor belt 66, and hence the seed cups 58 and respective seeds 48 deposited in each seed cup 58 pass through an internal passage 146 of the inline microwave resonance cavity 26'. Generally, as described above with regard to the microwave resonance cavity 26, the inline microwave resonance cavity 26' is structured and operable to accurately measure, or predict, the total mass of each seed 48 as it passes through the internal passage 146. The microwave resonance cavity 26 communicates the total mass data of each seed 48 to the central control system 34, where, via execution of the oil content analysis software, the central control system 34 records and saves the total mass data from each seed 48 and links or ties the total mass data to the respective seed 48 and the previously saved oil mass data for the respective seed 48.

More specifically, in such embodiments, the conveyor belt 62 passes through the internal passage 146 of the inline microwave resonance cavity 26' and the combined mass of conveyor belt 62, seed cup 58, and seed 48 is measured for each seed position. The belt plus the seed cup only mass for each seed position is tabulated prior to seed loading for each run and the seed 48 mass is inferred from the difference of the mass measured by the inline microwave resonance cavity 26' and belt/seed cup-only mass. In such embodiments the diverter assembly 30 is connected to the egress end 94B of the offload funnel 94 and is structured and operable as described above.

Referring to FIG. 8, in various embodiments, each seed cup 58 is structured and operable to help settle, center and retain each singulated seed 48 in a stable orientation within the respective seed cup 58 as and after each seed 48 is deposited into the respective seed cup 58, as described above. For example, in various embodiments, each seed cup 58 is formed to comprise a 3-dimensional (3D) diamond shaped reservoir 122 into which each respective seed 48 is deposited. The beveled and angled sides of the 3D diamond reservoir 122 cause each singulated seed 48 to be centered within the respective seed cup 58. Although the reservoir 122 is shown and described to be diamond shaped, it is envisioned that the reservoir 122 can be any other shape suitable to retain the seeds 48 within the seed cups 58 in a stable orientation during conveyance of the seeds 48 along the seed track 66 and through the NMR assembly 22. Additionally, in various embodiments, each seed cup 58 comprises a plurality of lateral slots, grooves or serrations 126 extending through the body of the respective seed cup 58, wherein the serrations 126 create sufficient friction between each respective seed 48 and the beveled and angled sides of the 3D diamond shaped (or other suitably shaped) reservoir 122 to reduce vibration of the respective seed 48 as the seed 48 and seed cup 58 travel along the conveyor track 66. More particularly, the 3D diamond shaped (or other suitably shaped) reservoir 122 and serrations 126 are structured and operable to stably retain the seeds 48 and reduce vibration of the seeds 48 such that the seeds 48 are prevented from 'bouncing' out of the seed cups 58 and are retained within the seed cups 58 in a stable orientation during conveyance of the seeds 48 along the seed track 66 and through the NMR assembly 22.

Figure 3A:
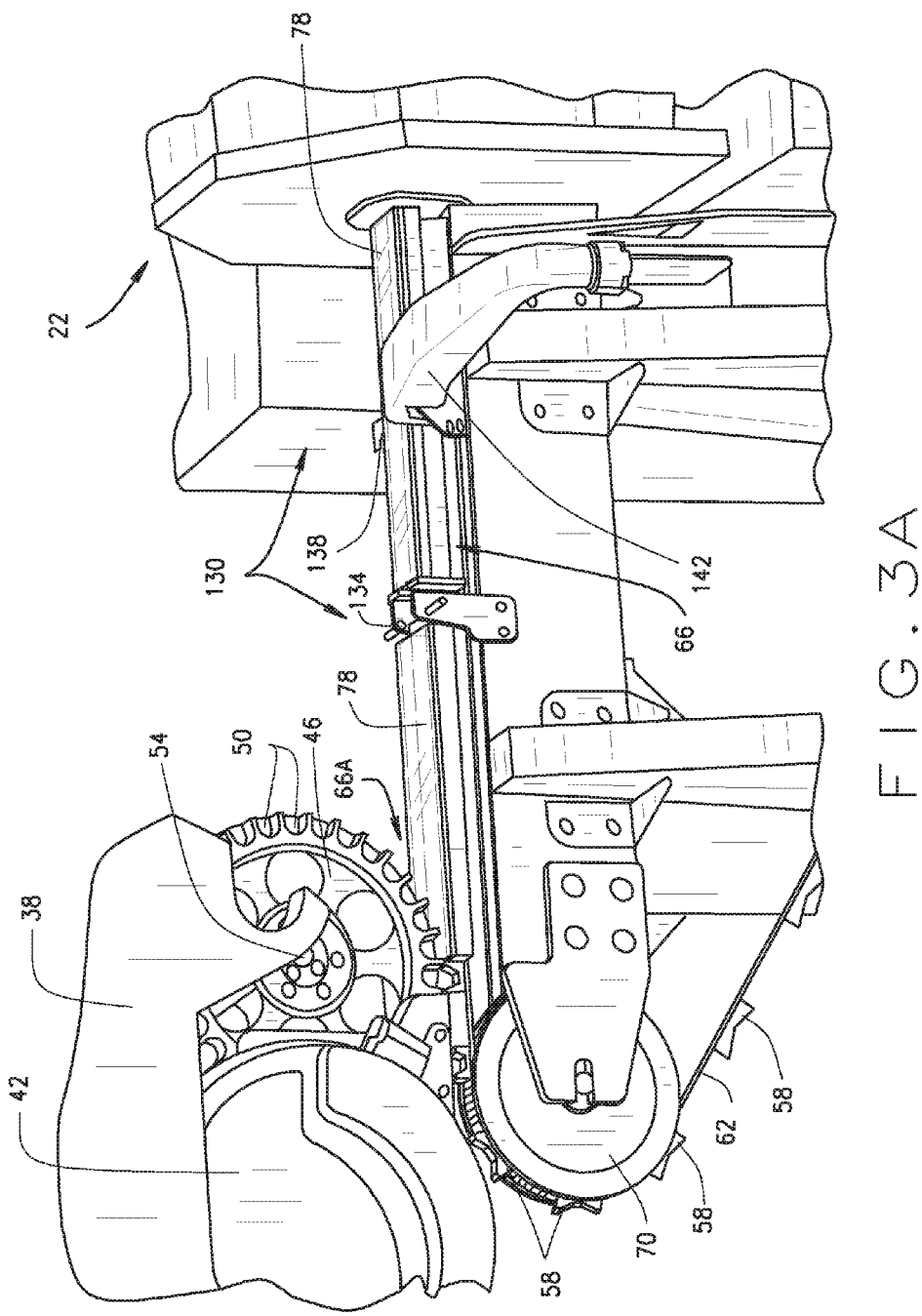
FIG. 3A is an isometric view of the small object feeder assembly shown in FIG. 2 and a proximal end of a small object conveyor assembly of the high throughput dynamic small object sorting system shown in FIG. 1, in accordance with various embodiments of the present disclosure.
Figure 3B:
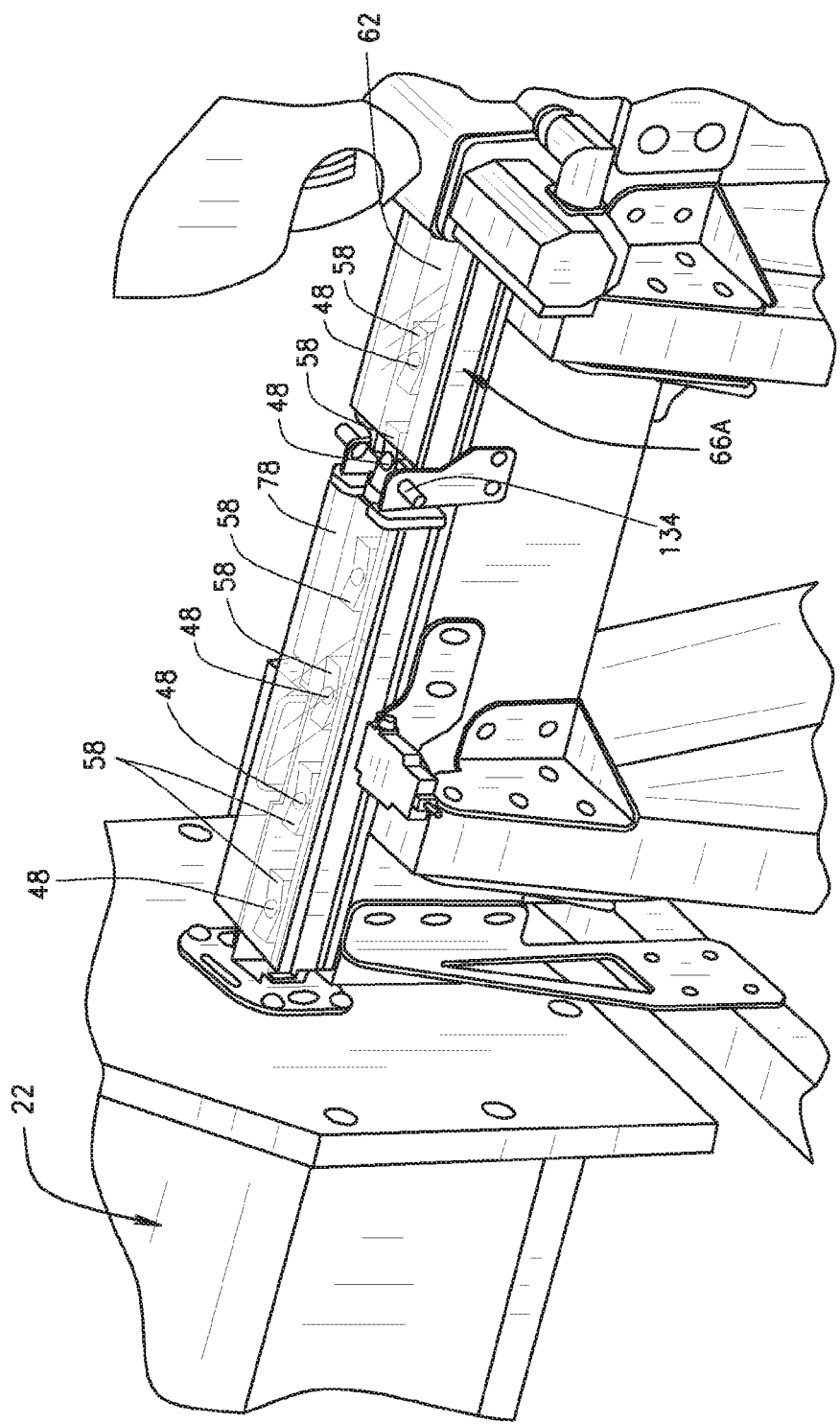
FIG. 3B is an isometric view of the proximal end of a small object conveyor assembly shown in FIG. 3A, in accordance with various embodiments of the present disclosure.

Referring now to FIGS. 3A and 3B, in various embodiments, the system 10 includes a stray seed removal assembly 130 that is structured and operable, as controlled by the central control system 34, to identify stray seeds 48 that, upon dispensing from the seed feeder assembly 14, have missed or fallen out of the respective seed cup 58, and consequently settle on the conveyor belt 62 between adjacent seed cups 58. In various embodiments, the stray seed removal assembly 130 includes a stray seed sensor 134 that is structured and operable to detect stray seeds 48 that have settled onto the conveyor belt 62 between adjacent seed cups 58. The stray seed sensor 134 communicates such detection of stray seeds 48 to the central control system 34. The stray seed removal assembly 130 additionally includes a stray seed expulsion device 138 disposed on a first side of the conveyor track 66 and a stray seed catch funnel 142 disposed opposite the stray seed expulsion device 138 on an opposing side of the conveyor track 66. The stray seed expulsion device 138 can be any device suitable to remove or expel each stray seed 48 from the conveyor belt 62 and deposit the removed or expelled stray seeds 48 into the stray seed catch funnel 142, whereby the removed or expelled stray seeds 48 are directed into a stray seed receptacle (not shown).

For example, in various implementations, the stray seed expulsion device 138 can be a pneumatic device that controls a lateral flow of air across the conveyer belt 62 to expel the stray seeds 48 from the conveyor belt 62 into the stray seed funnel 142. Particularly, in such embodiments, if a stray seed 48 is detected by the stray seed sensor 134, as the respective stray seed 48 passes in between the stray seed expulsion device 138 and the stray seed catch funnel 142, a valve of the pneumatic stray seed expulsion device 138 (as controlled by central control system 34) opens such that air is released that blows or expels the respective stray seed 48 off the conveyor belt 62 into the stray seed catch funnel 142, whereafter the respective stray seed 48 is directed into the stray seed receptacle.

Figure 7:
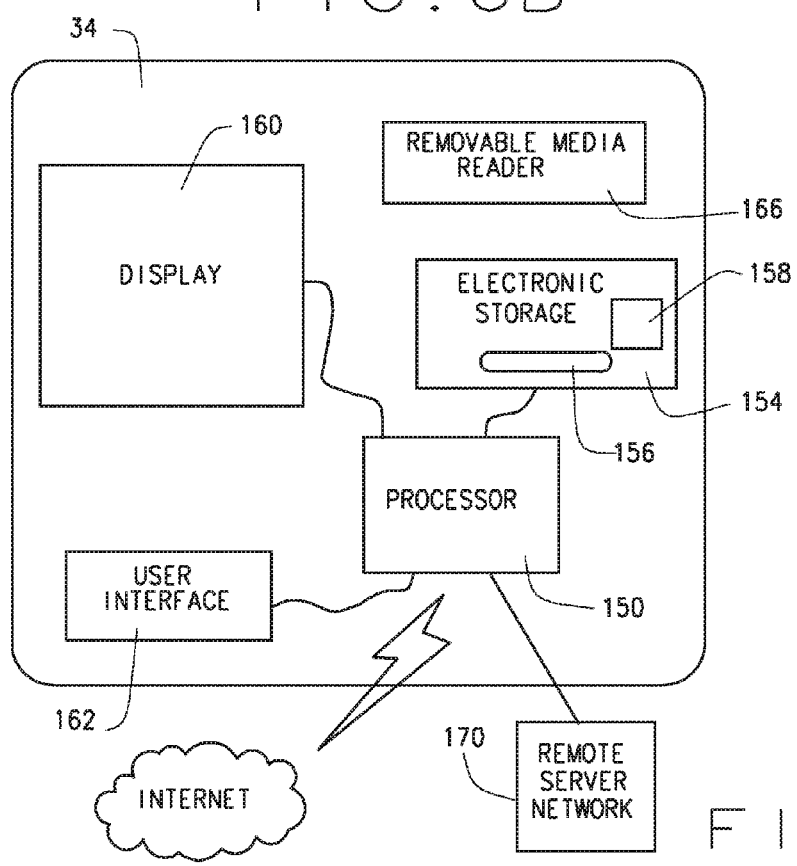
FIG. 7 is block diagram of a computer based central control system of the high throughput dynamic small object sorting system shown in FIG. 1, in accordance with various embodiments of the present disclosure.

Referring now to FIG. 7, in various embodiments, the central control system 34 is a computer based system that generally includes at least one processor 150 suitable to execute all software, programs, algorithms, etc., described herein to automatically, or robotically, control the operation of the high throughput dynamic seed sorting system 10, as described herein. The central control system 34 additionally includes at least one electronic storage device 154 that comprises a computer readable medium, such as a hard drive or any other electronic data storage device for storing such things as software packages or programs and algorithms 156 (e.g., the oil content analysis software), and for storing such things as digital information, data, look-up tables, spreadsheets and databases 158. Furthermore, the central control system 34 includes a display 160 for displaying such things as information, data and/or graphical representations, and at least one user interface device 162, such as a keyboard, mouse, stylus, and/or an interactive touch-screen on the display 158. In various embodiments the central control system 34 can further include a removable media reader 166 for reading information and data from and/or writing information and data to removable electronic storage media such as floppy disks, compact disks, DVD disks, zip disks, flash drives or any other computer readable removable and portable electronic storage media. In various embodiments the removable media reader 166 can be an I/O port of the central control system 34 utilized to read external or peripheral memory devices such as flash drives or external hard drives.

In various embodiments, the central control system 34, i.e., the processor 150 can be communicatively connectable to a remote server network 170, e.g., a local area network (LAN), via a wired or wireless link. Accordingly, the central control system 34 can communicate with the remote server network 170 to upload and/or download data, information, algorithms, software programs, and/or receive operational commands. Additionally, in various embodiments, the central control system 34 can be structured and operable to access the Internet to upload and/or download data, information, algorithms, software programs, etc., to and from internet sites and network servers.

In various embodiments, as described above, the central control system 34 includes the oil content analysis software, which is stored on the storage device 154 and executed by processor 150, and can further include one or more system control algorithms, or programs, stored on the storage device 154 and executed by processor 150. The oil content analysis software and other system control software are cumulatively identified in FIG. 7 by the reference numeral 156. It should be understood that although the central control system 34 has been sometimes described herein as directly controlling the various automated, or robotic, operations of the high throughput dynamic seed sorting system 10, it is execution of the oil content analysis software and other system control software, programs and/or algorithms by the processor 150, using inputs from the user interface 162 and various other components, sensors, systems and assemblies of the high throughput dynamic seed sorting system 10 that actually control the various automated, or robotic, operations of the high throughput dynamic seed sorting system 10 described herein.

Experimental Results

Experiments were performed utilizing the high throughput dynamic seed sorting system 10 to test the speed and accuracy of the high throughput dynamic seed sorting system 10 and methods for separating haploid seeds from diploid seeds. The experiments and results are described below Experiment No. 1

Experimental results using a first analysis method, e.g., a steady state free procession (SSFP) method, are as follows. For the following experiment, the RF probe 90 of NMR assembly 22 was configured as an 18 mm probe (Dead1=15 µs, Dead2=15 µs, and 90° pulse duration P90=4.9 µs) operating at 40° C., and the magnetic field strength generated by the NMR relaxometer 86 was set to 0.55 Tesla, corresponding to a 1H Larmor frequency of 23.4 MHz.

To test and optimize the data acquisition parameters, an artificial oil sample containing 0.3 g of tissue paper and 0.3 g of corn oil was used. To develop an oil calibration model for single seed corn samples, a set of 24 corn seeds with known oil content were used.

Figure 9A:
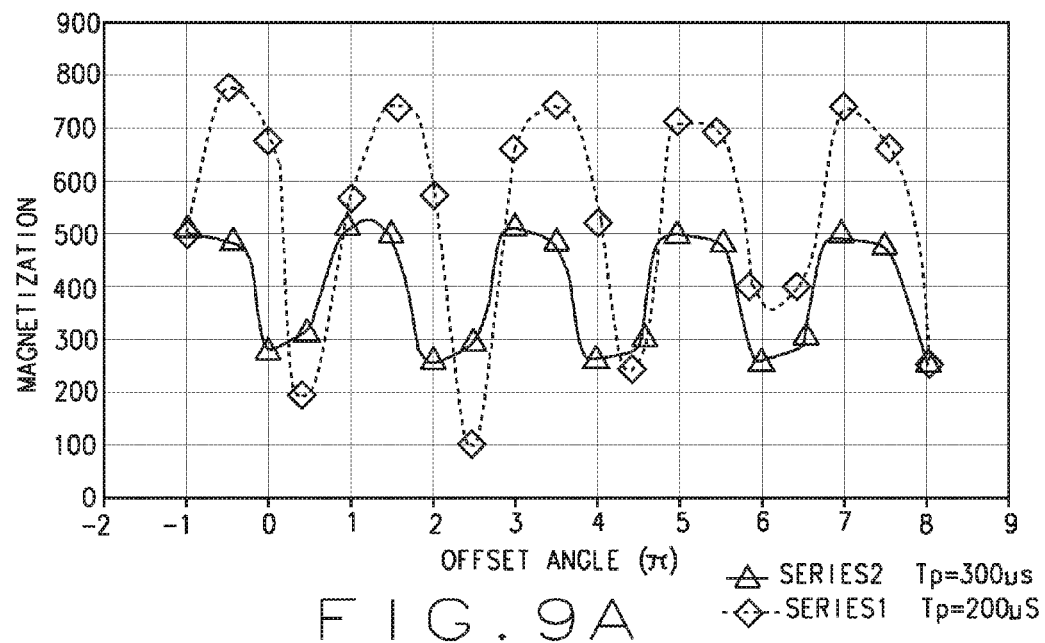
FIG. 9A is a graph illustrating the periodic dependence of a NMR magnetization signal on an offset O1, with two different Tp values, used during experiments utilizing the high throughput dynamic small object sorting system shown in FIG. 1, in accordance with various embodiments of the present disclosure.
Figure 9B:
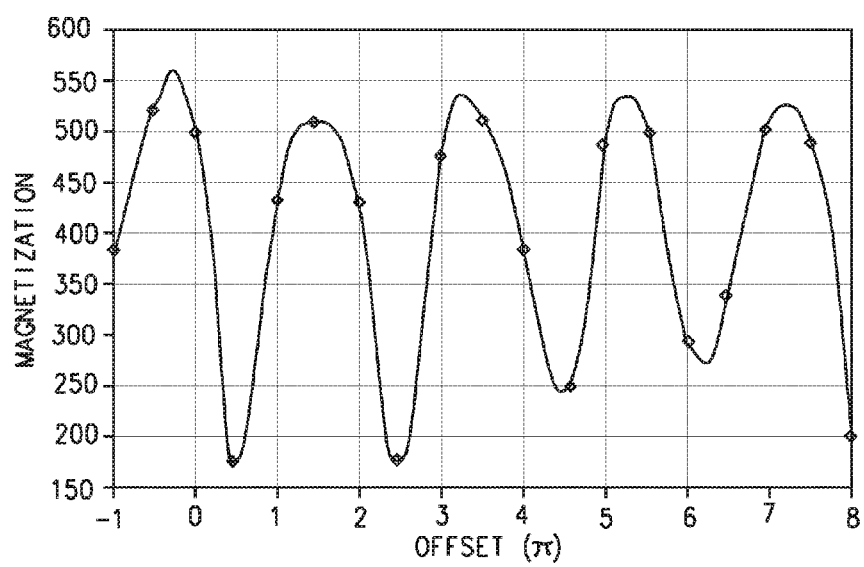
FIG. 9B is a graphical illustration similar to that shown in FIG. 8 performed on a single seed corn sample, in accordance with various embodiments of the present disclosure.

To obtain NMR signals with best signal-to-noise ratio, two key parameters need to be optimized. These parameters were the RF transmitter offset (O1) and the time interval between pulses (Tp). To find the optimal values of O1 and Tp, a series of experiments were performed with a set of different O1 and Tp values on the artificial oil sample. FIG. 9A shows the periodic dependence of NMR magnetization signal on the offset O1, with two different Tp values (100 µs and 300 µs). Similar experiments were also performed on a single corn seed sample and the results are shown in FIG. 9B. Based on these results, the offset O1 and time interval Tp were set to 3.37 and 100 µs, respectively, for subsequent quantitative oil calibration experiments.

Figure 10:
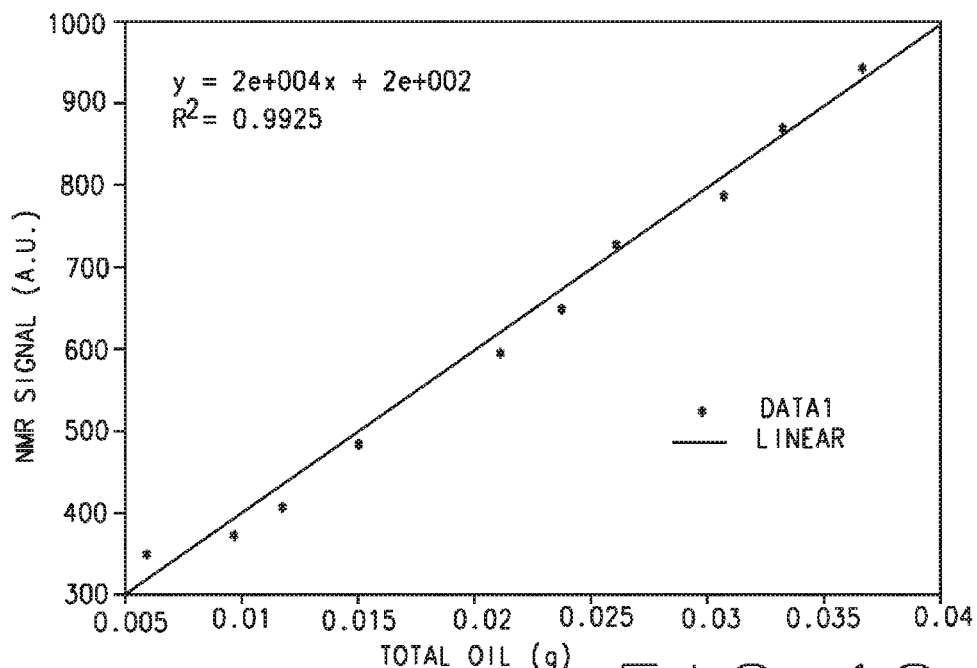
FIG. 10 is a graphical illustration demonstrating a correlation between the oil content (mass) and NMR signal amplitude generated during experiments utilizing the high throughput dynamic small object sorting system shown in FIG. 1, in accordance with various embodiments of the present disclosure.

To characterize the quantitative performance of the methods described herein for determination of oil content, a set of 11 artificial oil samples with oil mass varied from 5 mg to 40 mg were prepared, the amount of oil in each sample was measured using an analytical balance. The NMR methods described above were used to obtain the NMR signals of these samples. FIG. 10 demonstrates an excellent correlation between the oil content (mass) and the NMR signal amplitude. Particularly, FIG. 10 illustrates NMR signal versus oil mass of the artificial oil samples. Each sample was measured in triplicate and the standard deviations were used for the error bars. The small error bars in FIG. 10 indicates that the NMR signals are very reproducible.

Figure 11A:
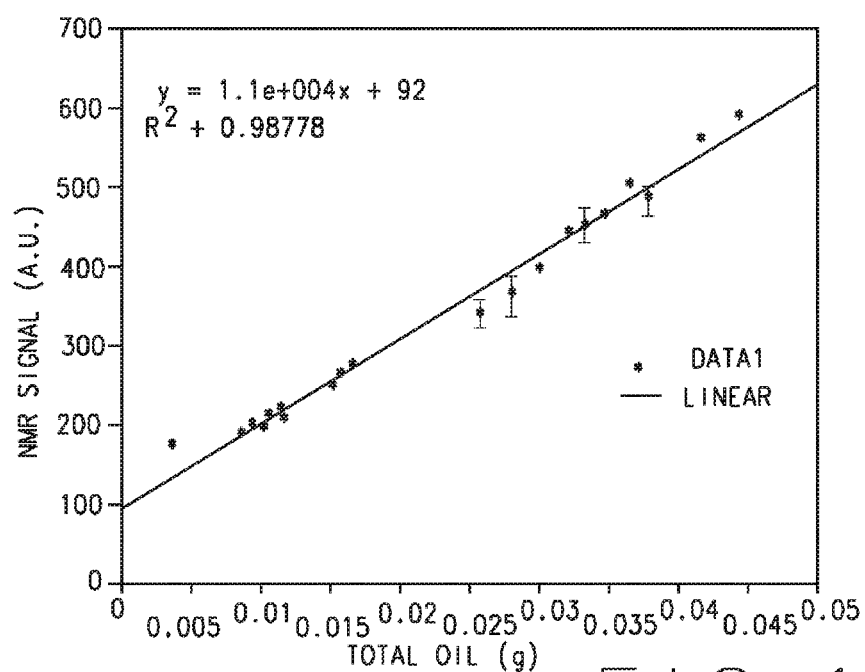
FIG. 11A is a graphical illustration showing signal amplitude as a function of total oil mass of the seed sample, during experiments utilizing the high throughput dynamic small object sorting system shown in FIG. 1, in accordance with various embodiments of the present disclosure.
Figure 11B:
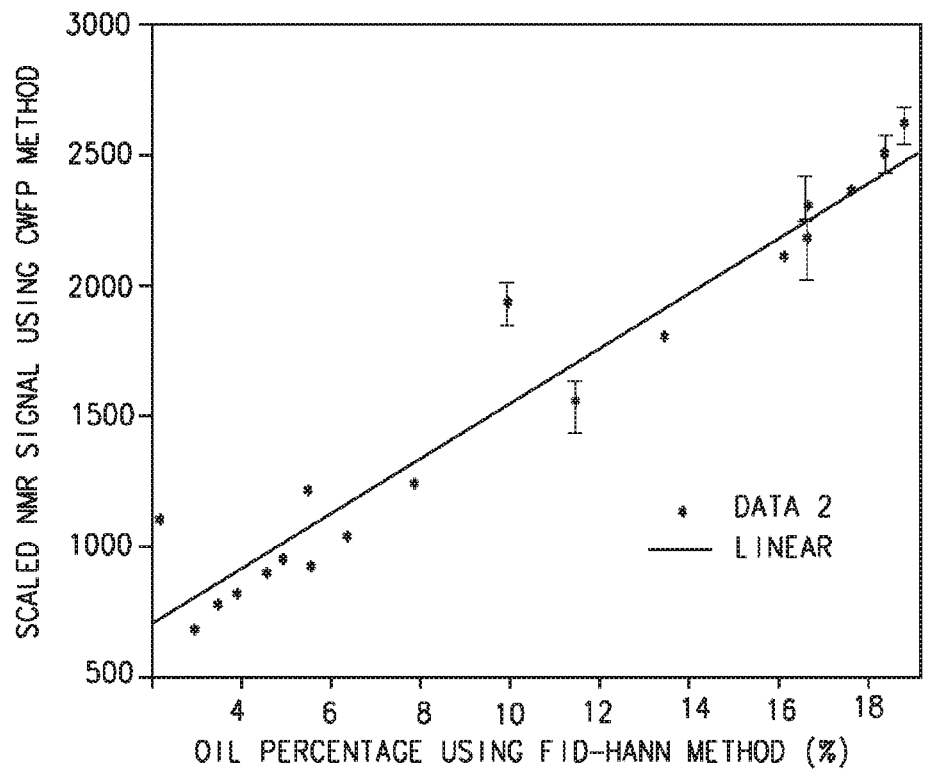
FIG. 11B is a graphical illustration showing signal amplitude per unit mass as a function of oil content (oil percentage) for seed samples during experiments utilizing the high throughput dynamic small object sorting system shown in FIG. 1, in accordance with various embodiments of the present disclosure.

It is important to develop a quantitative calibration model for determination of oil content in a single corn seed sample. A set of 24 single corn seed samples was prepared. The oil contents of these samples were previously determined using a conventional NMR method (FID-Hahn method) and the measured values were used as reference values to assess the performance of the experiments. The NMR signals were acquired with key NMR parameters: Tp=100 µs, O1=3.3π. FIG. 11A shows the signal amplitude as a function of total oil mass of the seed sample. FIG. 11B shows the signal amplitude per unit mass as a function of oil content (oil percentage) for seed sample. Each sample was measured in triplicate and the standard deviations were plotted as error bars in FIGS. 11A and 11B. The small error bar in FIGS. 11A and 11B indicate that the NMR signals utilizing the high throughput dynamic seed sorting system 10 have good reproducibility.

Figure 12:
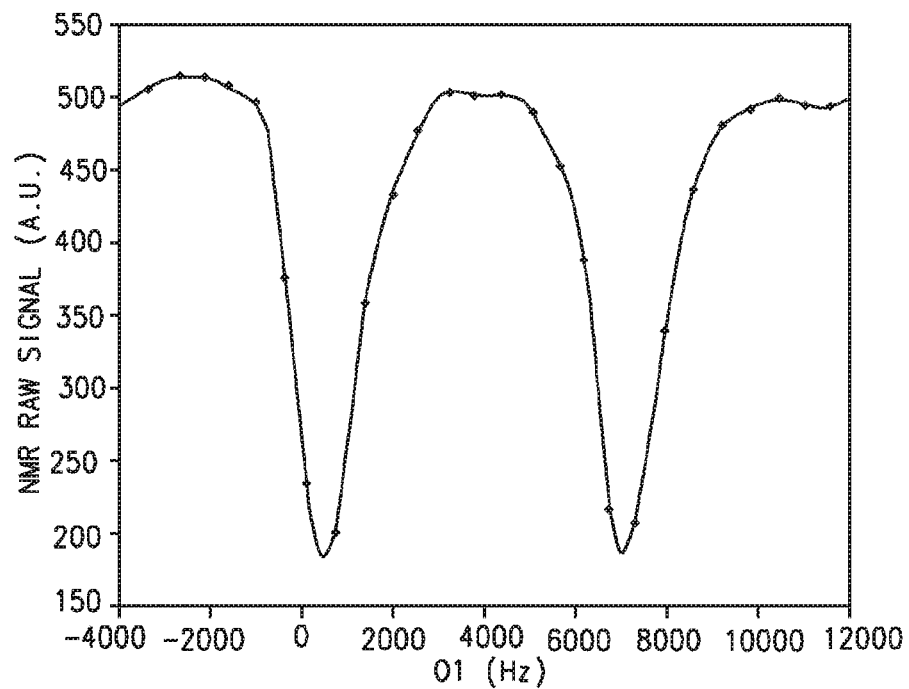
FIG. 12 is a graphical illustration showing where an O1 frequency offset was plotted against the NMR signal, the NMR signal varies periodically with different O1 values, during experiments utilizing the high throughput dynamic small object sorting system shown in FIG. 1, in accordance with various embodiments of the present disclosure.

Since the primary application of the high throughput dynamic seed sorting system 10 and methods described herein are for diploid/haploid seed sorting by measuring the oil content of single seed, the system 10 and methods need to be optimized for the type of seed will be encountered in real sorting application. The method optimization includes pulse interval (Tp) adjustment and receiver frequency offset (O1) optimization. For Tp adjustment, Tp was adjusted to 150 µs to allow the center of NMR signal at each pulse interval to be acquired. For O1 optimization, the NMR measurement is done on a single seed. A sequence of O1 values was applied and the corresponding NMR signals were measured. As shown in FIG. 12, where the O1 frequency offset was plotted against the NMR signal, the NMR signal varies periodically with different O1 values. The optimal O1 value was set to 3800 Hz (or offset angle π) because at this O1 value, the largest NMR signal amplitude was obtained.

Because the oil range of real diploid/haploid seeds is smaller than that of the previous calibration sample set (24 seeds), to ensure best measurement accuracy, a new NMR calibration was developed using the real diploid/haploid seeds. A set of 36 diploid/haploid seeds were used to develop a new calibration model. For each seed, the oil content (in percentage) was measured by a traditional NMR method and the mass was determined by an analytical balance. The reference total oil contents (oil mass) were calculated by multiplying the oil percentage with the mass of seed. The experiment was performed utilizing the system 10 to acquire NMR signal of each seed. For each seed, the measurements were repeated 3 times to assess the measurement reproducibility (analytical precision).

Figure 13A:
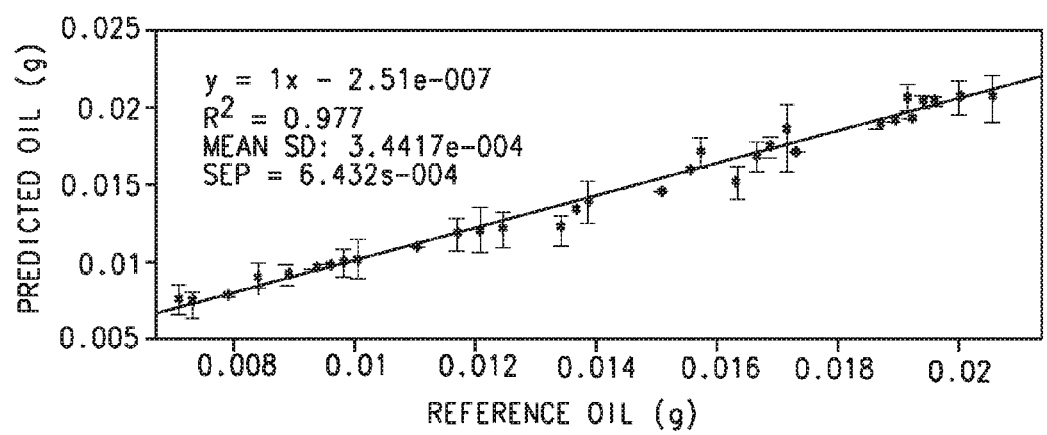
FIG. 13A is a graphical illustration showing reference oil weight (in gram) versus predicted oil weight (in gram) of a set of 36 calibration samples (real diploid/haploid seeds), during experiments utilizing the high throughput dynamic small object sorting system shown in FIG. 1, in accordance with various embodiments of the present disclosure.
Figure 13B:
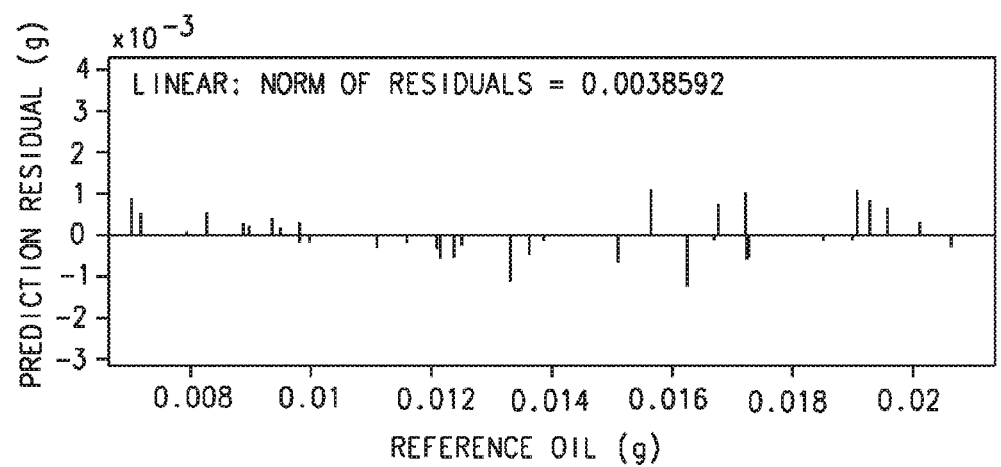
FIG. 13B is a graphical illustration showing prediction residual for each sample shown in FIG. 13A, in accordance with various embodiments of the present disclosure.

To further improve the measurement reproducibility, the single seed was constrained at the center of the NMR assembly 22 by placing the seed on the top of a sample holder in the NMR assembly 22, while the orientation of the seed was changed at each measurement. A univariate calibration model was developed by correlating the reference total oil content with NMR signal (mean value of the 3 repeat measurements). The plot of reference oil vs. prediction oil and the plot of prediction residuals are shown in FIGS. 13A and 13B. The calibration model shows that there exists a very good correlation between reference oil mass and predicted oil mass ($R2=0.977$, standard error of calibration SEC=0.64 mg) and that the measurement reproducibility is very good (mean standard deviation=0.34 mg).

Figure 14A:
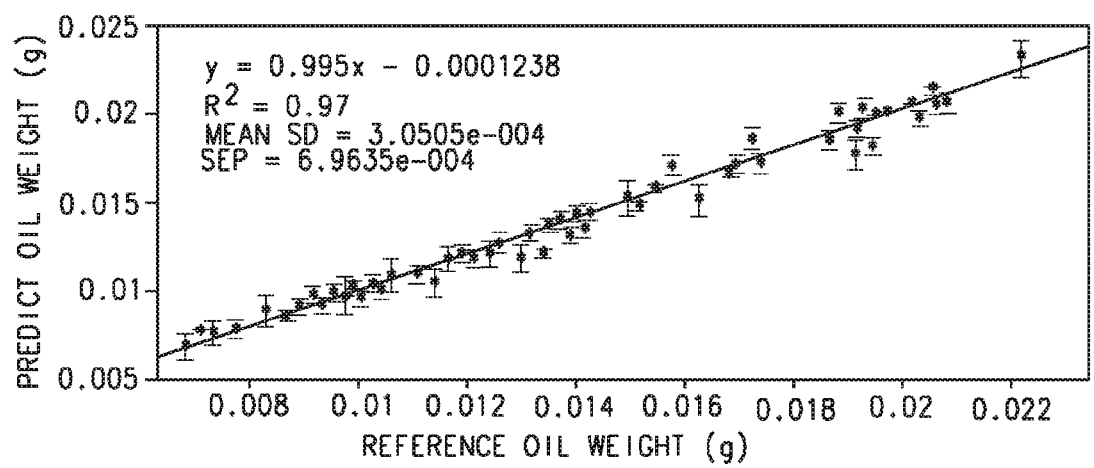
FIG. 14A is a graphical illustration showing reference oil weight (in gram) versus predicted oil weight (in gram) of a set of 78 validation samples (real diploid/haploid seeds), during experiments utilizing the high throughput dynamic small object sorting system shown in FIG. 1, in accordance with various embodiments of the present disclosure.
Figure 14B:
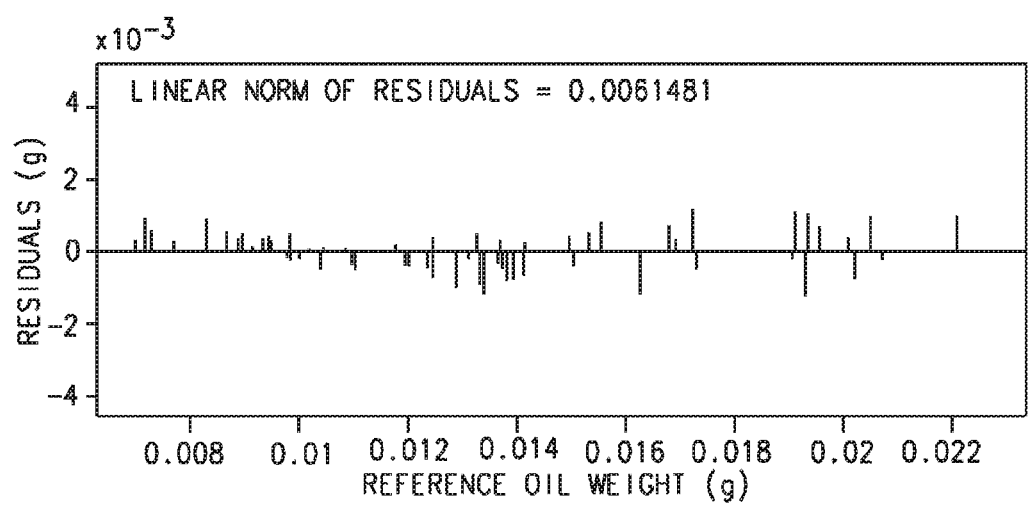
FIG. 14B is a graphical illustration showing prediction residual for each sample shown in FIG. 14A, in accordance with various embodiments of the present disclosure.

To validate the NMR calibration, a set of 78 diploid/haploid seeds were used. The reference oil weights of these seeds were determined as described previously. As shown in FIGS. 14A and 14B, using the new calibration model, the oil content can be predicted with great accuracy ($R2=0.97$, standard error of prediction SEP=0.69 mg) and good precision (mean standard deviation=0.3 mg).

Figure 15:
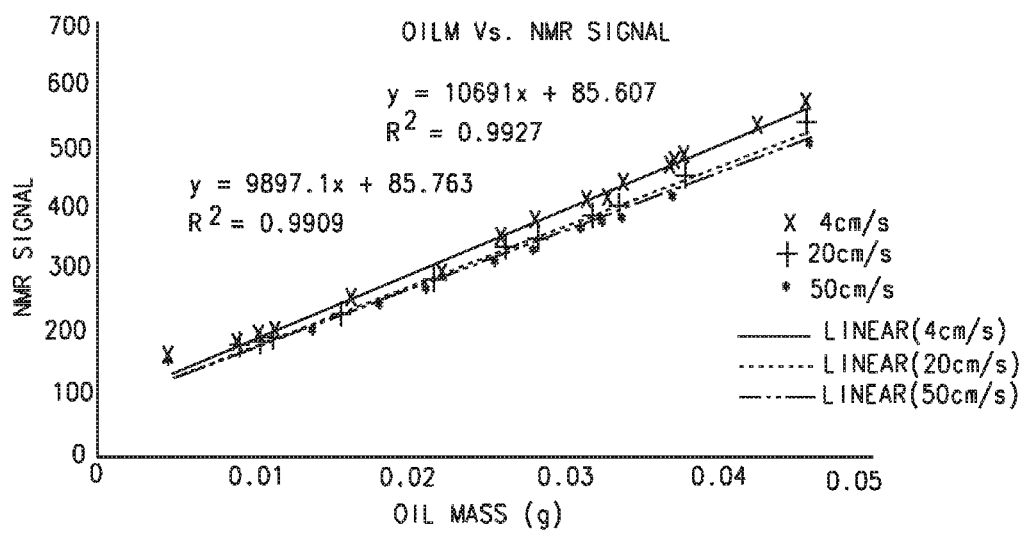
FIG. 15 is a graphical illustration showing the correlation between oil mass and NMR signal for seed traveling at various speeds, during experiments utilizing the high throughput dynamic small object sorting system shown in FIG. 1, in accordance with various embodiments of the present disclosure.
Figure 16:
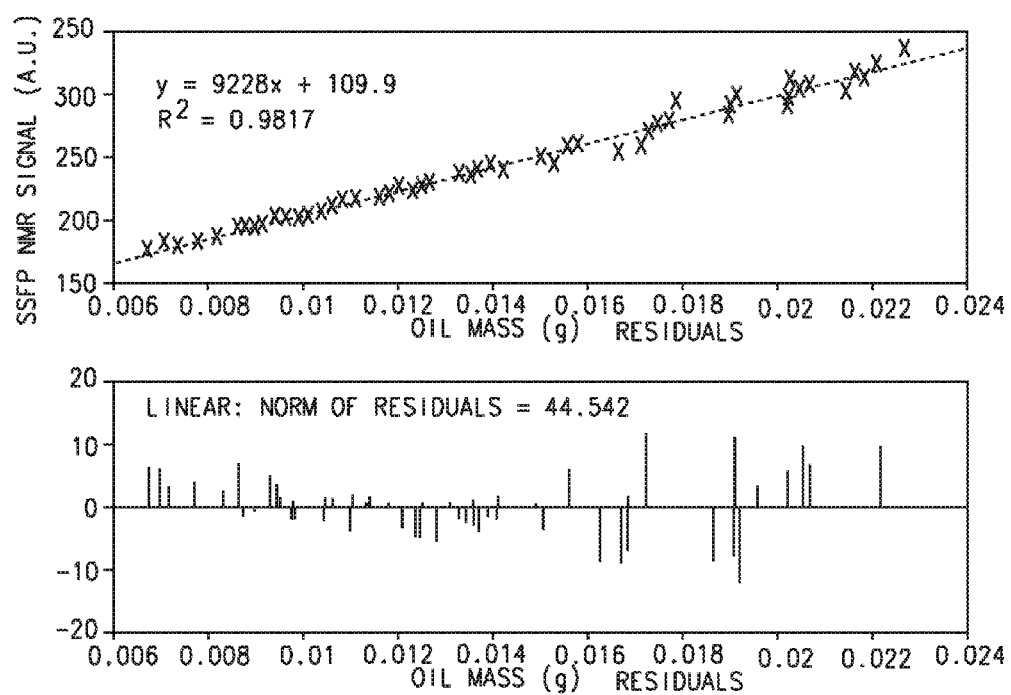
FIG. 16 is a graphical illustration showing that a validation study with 78 doubled haploid seeds showed good correlation ($R^2=0.982$) between NMR signal and oil mass, during experiments utilizing the high throughput dynamic small object sorting system shown in FIG. 1, in accordance with various embodiments of the present disclosure.

In one embodiment, a dual-magnet NMR system that consists of two identical 0.5 Tesla magnets, one used as prepolarization magnet and another used as measurement magnet, was constructed. An automated high-speed linear convey system was connected to the NMR system to deliver corn seeds at speed up to 50 cm/s. A position trigger was mounted on the conveyor track to trigger the NMR pulse at precise sample position. A set of 24 seeds were used to test the performance of the high-speed NMR prototype with sample moving at various speeds. FIG. 15 shows the correlation between oil mass and NMR signal for seed traveling at various speeds. A set of 78 double haploid seeds were used to validate the performance of the system. These samples were moving at a speed of 50 cm/s. FIG. 16 illustrates that the validation study with 78 doubled haploid seeds showed good correlation ($R^2=0.982$) between NMR signal and oil mass.

In conclusion, the experiments described above demonstrate that the high throughput dynamic seed sorting system 10 and methods described herein provide a very useful analytical system and method for rapid and quantitative determination of oil content in single seed samples. Under the optimal parameters, a linear relationship between the NMR signal and oil content can be found for seed samples. It was also shown that a successful calibration model was developed for determining the oil content in real diploid/haploid corn seeds. The NMR method was validated on a large set of samples (78 diploid/haploid seeds) under high-speed and continuous measurement condition, and the result demonstrated that the high throughput dynamic seed sorting system 10 is able to determine the oil content in single seed with great accuracy and precision. Additionally, as described above, due to the improvement of signal-to-noise ratio this NMR method, the measurement time for each single seed sample can be as short as 20 ms. Thus, the high throughput dynamic seed sorting system 10 and methods described herein allow for single seed samples to be analyzed in an automated and continuous fashion.

Experiment No. 2

Figure 17A:
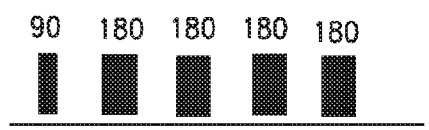
FIG. 17A is a graphical illustration of a 'single-shot' pulse sequence implemented by the high throughput dynamic small object sorting system shown in FIG. 1, in accordance with various embodiments of the present disclosure.
Figure 17B:
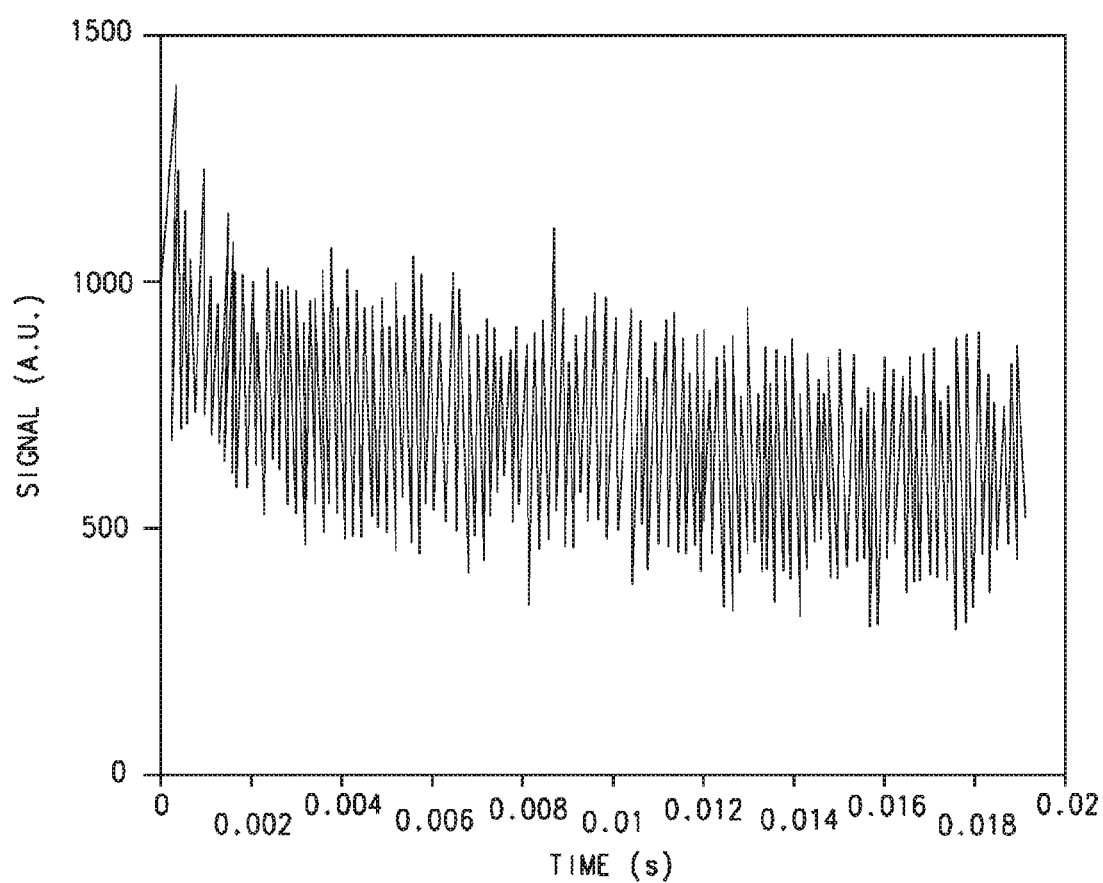
FIG. 17B is a graphical illustration of signal generated for a corn seed utilizing the 'single-shot' pulse sequence implemented by the high throughput dynamic small object sorting system shown in FIG. 1, in accordance with various embodiments of the present disclosure.

Experimental results using a second analysis method are as follows. In order to reach an analytical throughput of more than 20 seeds per second, seed samples can only pass through the NMR assembly 22 once with a travel speed of more than 100 cm per second. Because each sample travels through the NMR assembly 22 only once, there is no possibility of using a traditional NMR pulse sequence that scans a static sample multiple times. The methods of the present high-throughput measurement must be 'single-shot'. Therefore, in various embodiments, the high throughput dynamic seed sorting system 10 described above can implement a single-shot method that generates a pulse sequence that comprises a 90 degree pulse followed by a train of 180 degree pulses, as shown in FIG. 17A. As shown in FIG. 17B, for a seed sample, the single-shot signal contributed by moisture (water) component decays completely after 2 ms, the later part of single-shot signal is mainly contributed by oil component. By averaging the later part of single-shot signal, a linear relationship can be established between the averaged NMR signal and oil content.

Figure 18:
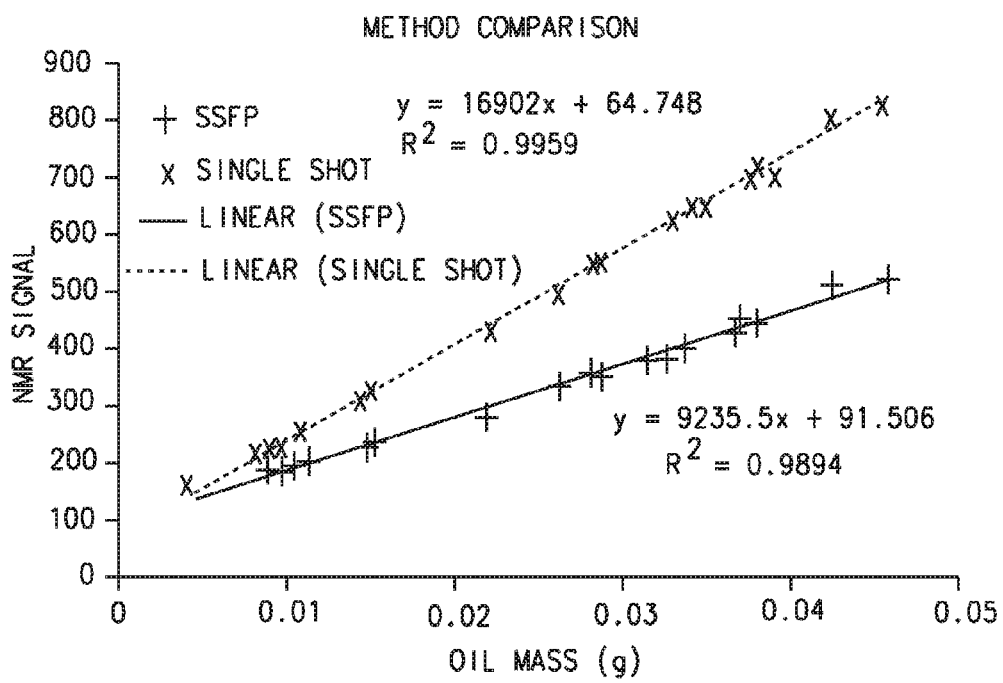
FIG. 18 is a graphical illustration showing a comparison of calibration curves implementing the by the high throughput dynamic small object sorting system shown in FIG. 1, using as single-shot analysis method and SSFP analysis method, in accordance with various embodiments of the present disclosure.

Referring now to FIG. 18, to test the single-shot analysis method, a set of 24 seed samples with oil content varying from 3 mg to 50 mg were used as a calibration set to evaluate the correlation between the single-shot signals and oil content. The single-shot NMR measurement was utilizing the high throughput dynamic seed sorting system 10, with the samples traveling through the NMR assembly 22 at a speed of 50 cm per second. Each sample was measure 3 times and the standard deviation of NMR signal was plotted as error bar in the calibration curve. The calibration curve using single-shot method was compared with that using SSPF method, as shown in FIG. 18.

Figure 19:
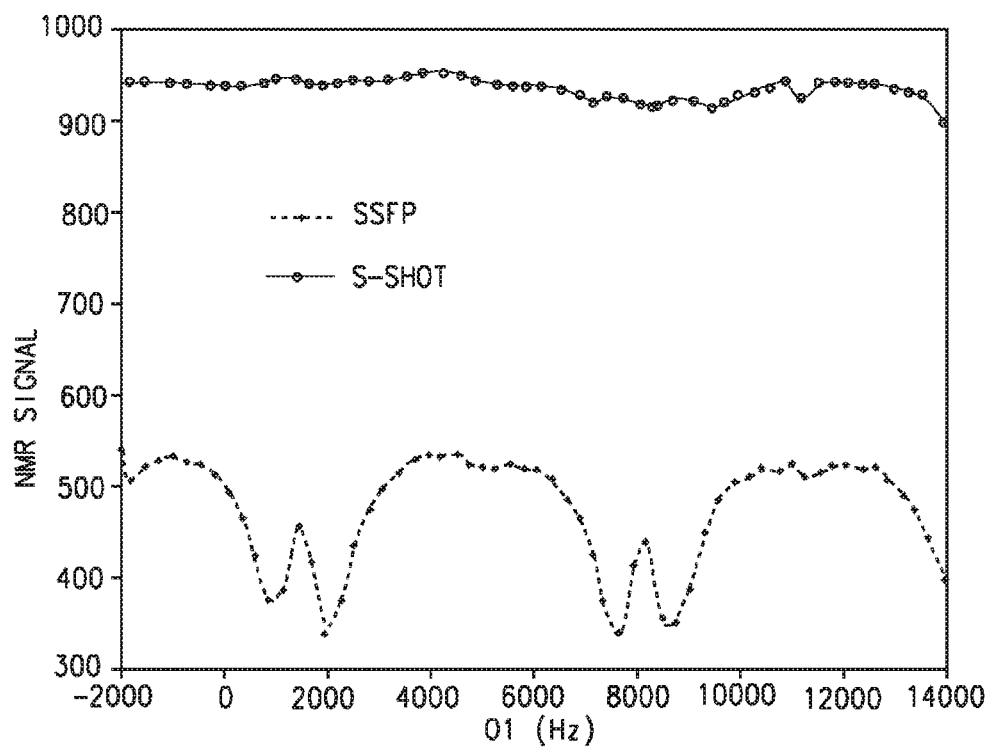
FIG. 19 is a graphical illustration showing a comparison of magnetic field dependency implementing the by the high throughput dynamic small object sorting system shown in FIG. 1, using as single-shot analysis method and SSFP analysis method, in accordance with various embodiments of the present disclosure.

In addition to the superior signal to noise ratio (S/N) and better analytical performance, the single-shot method is more robust than the SSFP method. The single-shot signal is less dependent on magnetic field uniformity in comparison to the SSFP method. FIG. 19 shows the dependency of the single-shot and the SSFP signals on the field fluctuation. Because the single-shot method has better tolerance of magnetic field fluctuation, it makes the magnetic field stability problem less important and allows less expensive magnet to be used in the NMR assembly 22.

Figure 20:
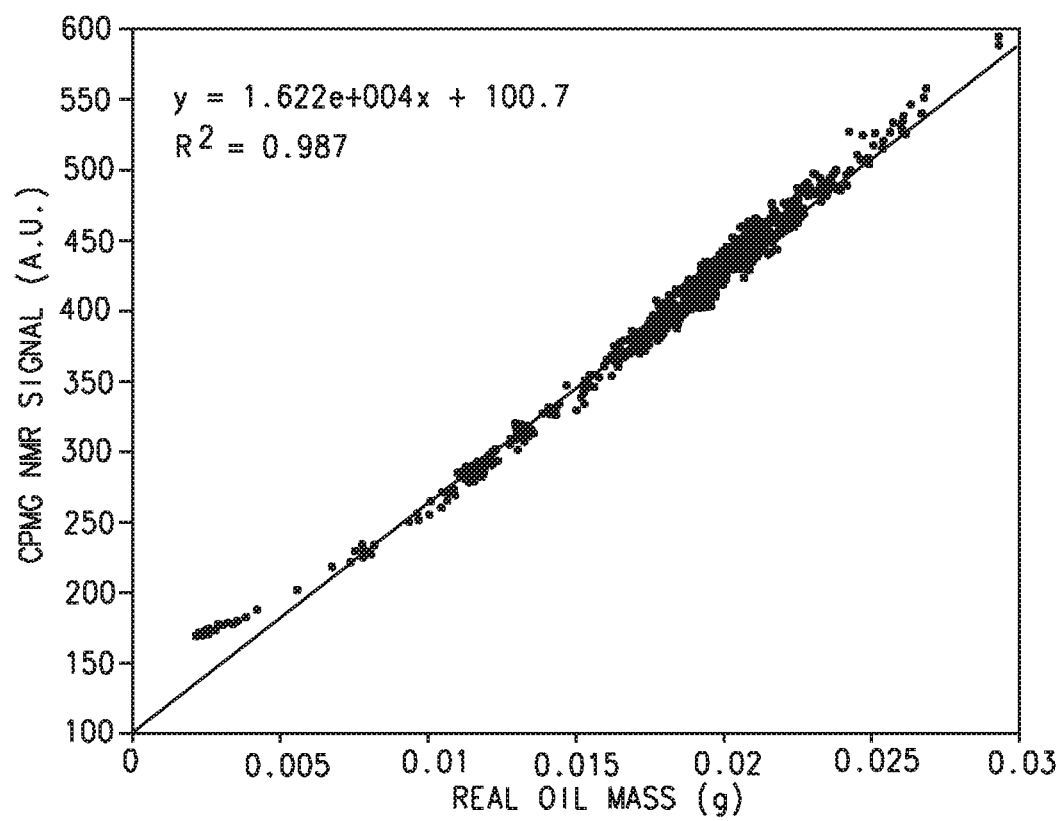
FIG. 20 is a graphical illustration showing a correlation between a single-shot analysis NMR signal and oil mass implementing the by the high throughput dynamic small object sorting system shown in FIG. 1, in accordance with various embodiments of the present disclosure.
Figure 21:
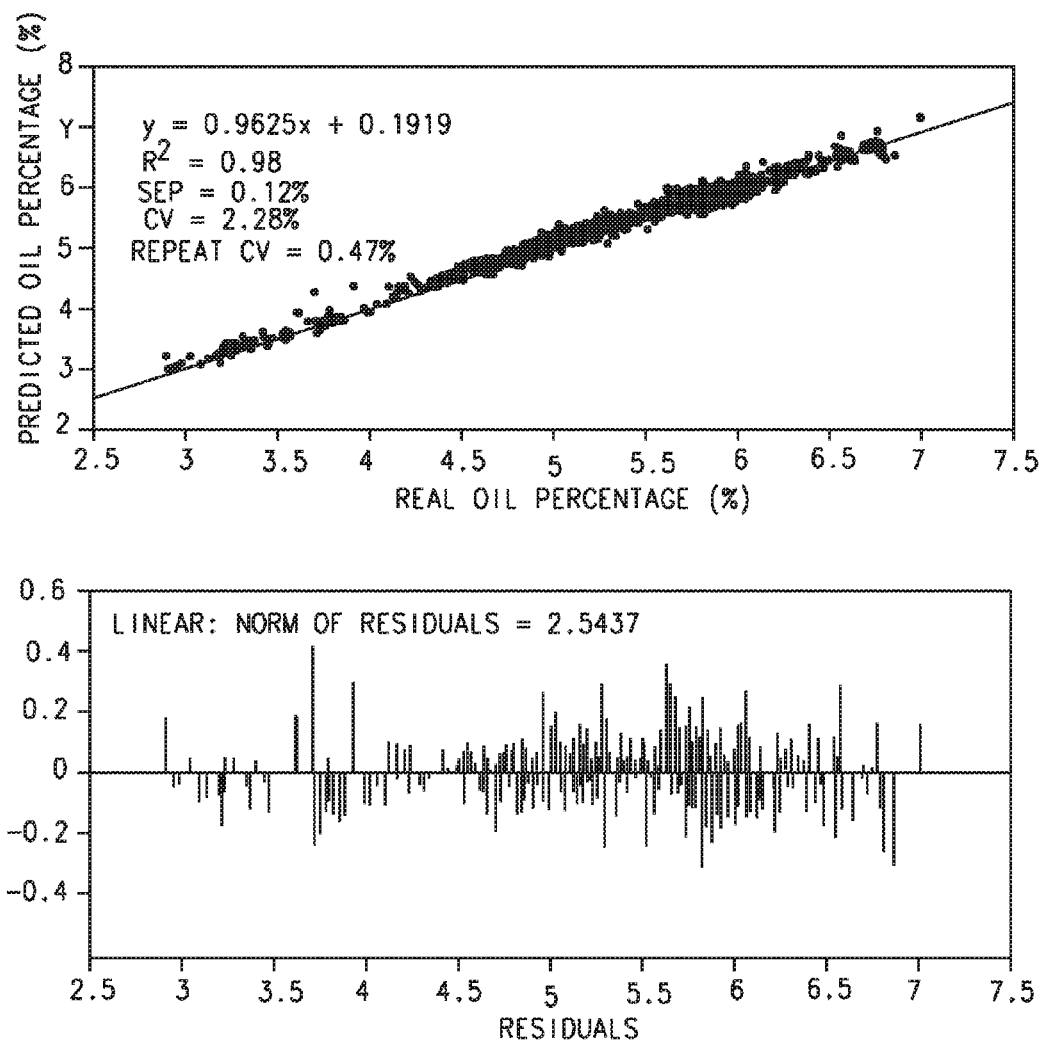
FIG. 21 is a graphical illustration showing the data of FIG. 20 when samples with extremely low oil content are removed, in accordance with various embodiments of the present disclosure.

To further validate the performance of single-shot method for quantitative determination of oil content, a set of 480 corn seeds, including both diploid and haploid seeds, were tested using the high throughput dynamic seed sorting system 10 with the samples traveling through the NMR assembly 22 at a speed of 50 cm per second. FIG. 20 shows the correlation between single-shot NMR signal and oil content. FIG. 21 shows the percentage based calibration curve using single-shot method.

Hence, as described above, the single-shot method was tested and validated for nondestructive and high-throughput determination of oil content in single seed. And, based on the results, as described above, the single-shot method is an excellent analytical method in terms of accuracy and precision. In addition, compared to the SSFP method, the single-shot method is more sensitive and robust.

Additionally, although the high throughput dynamic seed sorting system 10 has been described above to use oil mass and seed mass to compute the oil content as marker to obtain superior separation between haploid and diploid seed. It is also envisioned that good separation of haploid and diploid seed can be achieved utilizing the high throughput dynamic seed sorting system 10 to obtain only the oil mass data without the seed mass data. Hence, in such embodiments, the microwave resonance cavity 26 would not be included in the high throughput dynamic seed sorting system 10.

Experiment No. 3

Figure 22:
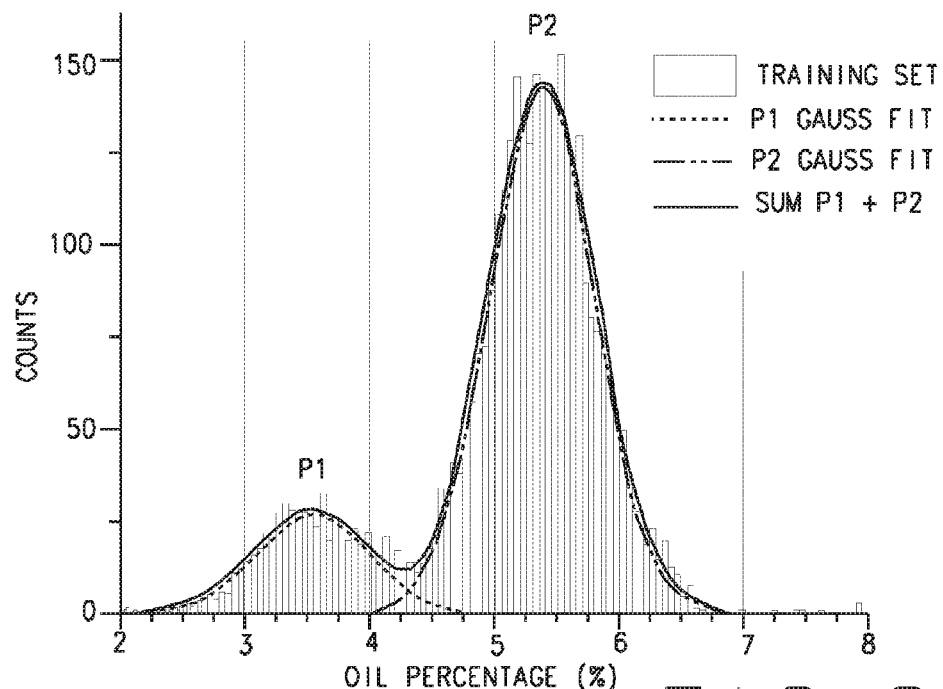
FIG. 22 is a graphical illustration of a typical bimodal distribution of oil percentage with Gaussian least-squares curve fitting results overlaid with the peaks labeled as "P1" and "P2", in accordance with various embodiments of the present disclosure.

Experimental results of the high throughput dynamic seed sorting system 10 operating under typical production conditions with representative material are now discussed. Sixty distinct seed populations consisting of a mixture of haploid and diploid seeds 48 were sorted utilizing the system 10 by first running a training set subsample for each population. A histogram of oil content for each training set was generated and curve fit using a least-squares fit of the Normal (i.e., Gaussian) Distribution to identify the haploid and diploid components of the population. A typical result of the bimodal oil percentage distribution is shown in FIG. 22 with two Gaussian fits from the least-squares routine overlaid and labeled "P1" and "P2". Peaks "P1" and "P2" in FIG. 22 are assigned as putative haploids and putative diploids, respectively.

Figure 23:
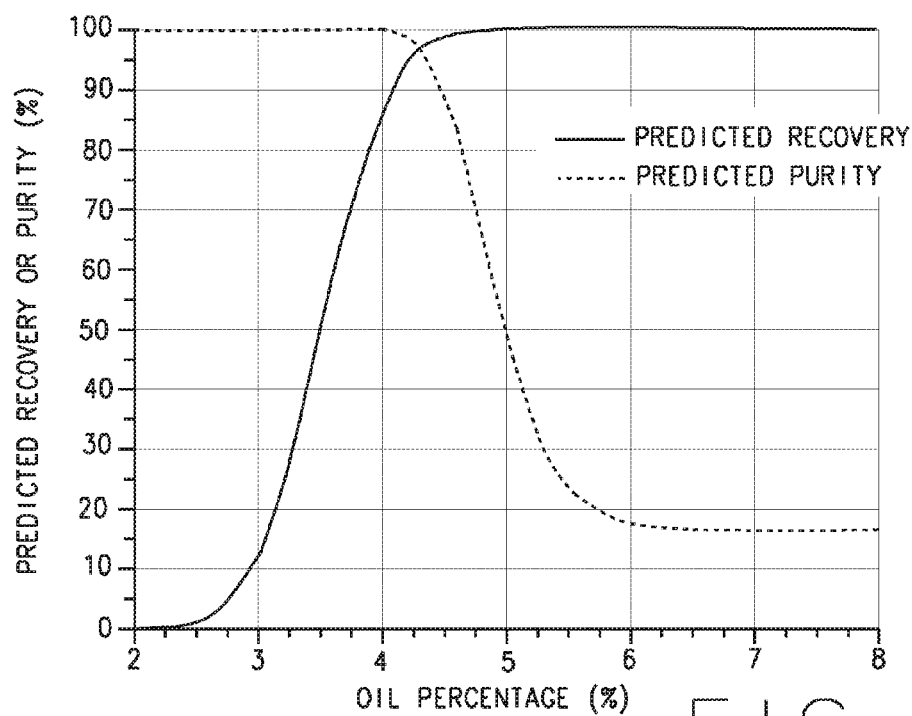
FIG. 23 is a graphical illustration of haploid recovery and haploid purity vs. oil percentage sorting threshold estimated from numerical integration of peaks "P1" and "P2", in accordance with various embodiments of the present disclosure.

Haploid recovery (i.e., haploids selected relative to the total estimated haploids present) and haploid purity (i.e., ratio of haploid seeds to the total seed 48 count in the low oil container) can be estimated from the results of Gaussian curve fitting and the result for the typical peak fitting shown in FIG. 22 is shown in FIG. 23. Haploid recovery for a given oil percentage sorting threshold is calculated by numerical integration of "P1" in FIG. 22 through the sorting threshold normalized to the total integrated area of "P1". Haploid purity for a given oil percentage sorting threshold is calculated by numerical integration of "P1" in FIG. 22 normalized to the numerical integration of the sum of peaks "P1" and "P2" of FIG. 22. In various embodiments, the calculated haploid recovery and haploid purity can be corrected for estimated or measured machine sorting errors whereby seeds 48 selected for expulsion by the stray seed removal assembly 130 are unintentionally discarded and seeds 48 not selected for expulsion by the stray seed removal assembly 130 inadvertently bounce into the stray seed catch funnel 142.

Figure 24:
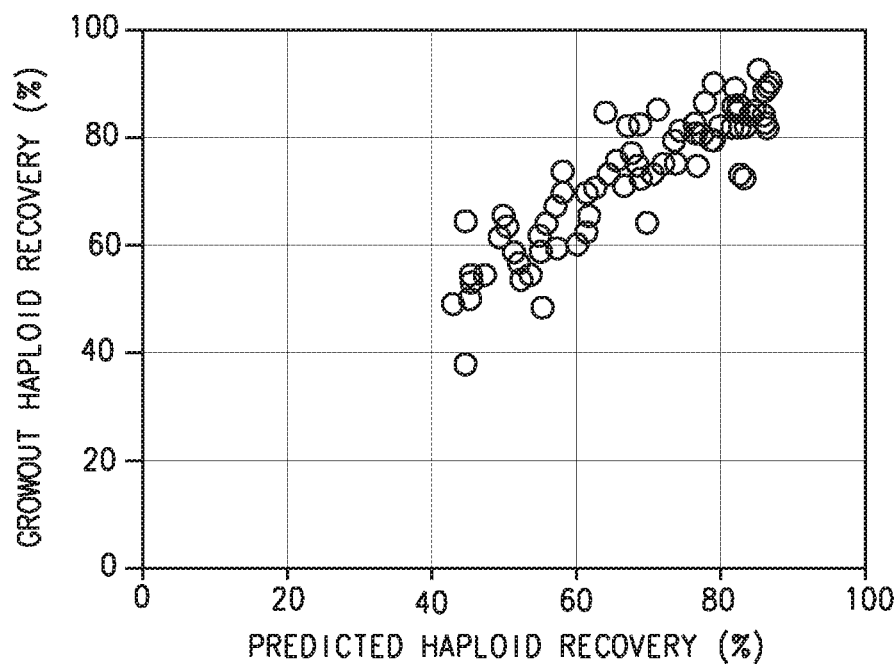
FIG. 24 is a graphical illustration showing a correlation for 60 distinct populations between haploid recovery measured by field growout data and predicted haploid recovery from Gaussian curve fitting of a population-specific training set, in accordance with various embodiments of the present disclosure.
Figure 25:
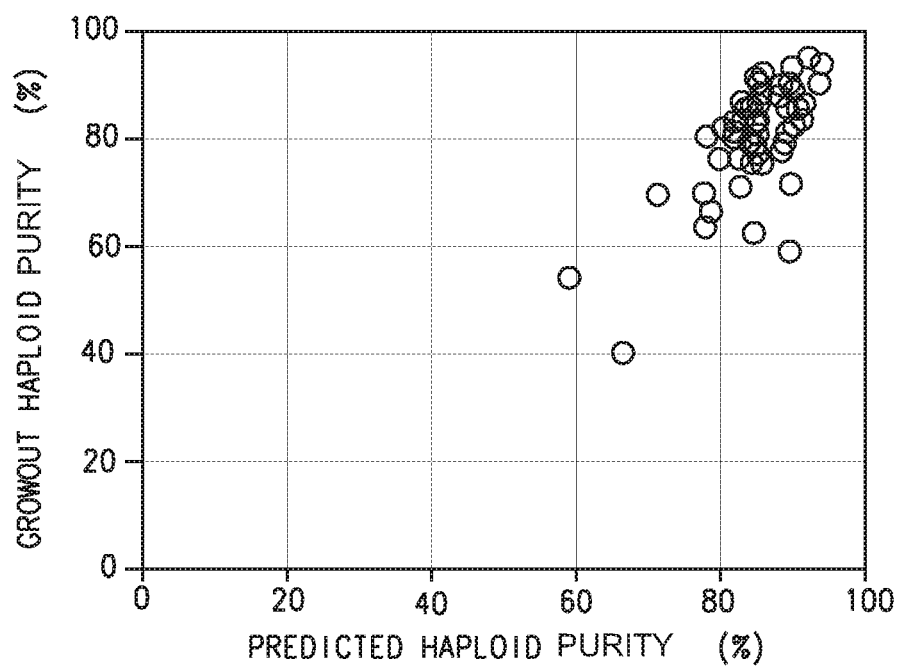
FIG. 25 is a graphical illustration showing a correlation for 60 distinct populations between haploid purity measured by field growout data and predicted haploid purity from Gaussian curve fitting of a population-specific training set, in accordance with various embodiments of the present disclosure.

For the present experiment, oil sorting thresholds were selected among the complete set of populations to represent a range of predicted haploid recovery and predicted haploid purity. Complete samples or subsamples of both sorted categories were planted in the field for each population in designated plots. After six weeks of growth, emerged individual plants were phenotypically scored for ploidy by observing the height of the plant relative to the other plants in the plot. Diploid plants show pronounced differences in height, leaf area, and vigor relative to their haploid counterparts, and diploid contamination in the putative haploid plot can be estimated by accounting (i.e., eliminating, removing or reclassifying) for plants which were classified as seeds to be haploid, but were later determined to be diploid plants based on their phenotype at approximately six weeks of growth. Similarly, by counting the smaller and less vigorous members of the putative diploid plot, the rate of seeds mistakenly classified as haploid can be estimated. Using this scoring method, haploid recovery can be estimated by calculating the fraction of recovered haploids to the total, with appropriate weighting (if subsampling was used). Haploid purity can be estimated by calculating the ratio between the final number of haploids detected to the total number of seeds in the putative haploid plot. Both results are then compared with the predicted values to demonstrate the ability to accurately predict haploid recovery and purity rates using an oil sorting threshold selected from the curve fitting results for a training set for an arbitrary population. FIGS. 24 and 25 show the observed vs. predicted haploid recovery and haploid purity, respectively, for the 60 test populations.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A high throughput dynamic seed sorting system, said system comprising:
    a conveyor assembly including a seed conveyor belt having a plurality of seed cups attached thereto, the conveyor assembly structured and operable to continuously move the conveyor belt at a selected constant rate of speed during operation of the system;
    a seed feeder assembly structured and operable to singulate seeds from a plurality of seeds and deposit each singulated seed into a respective one of the seed cups as the conveyor belt continuously moves at the selected constant rate of speed;
    a nuclear magnetic resonance (NMR) assembly having the conveyor belt operably extending therethrough, the NMR assembly structured and operable to generate oil mass data for each seed as each seed moves through the NMR assembly at the selected constant rate of speed; and
    a computer based central control system structured and operable to:
    receive the oil mass data from the NMR assembly for each seed, and execute oil content software to:
        store the oil mass data for each seed and associate the oil mass data received for each seed with the respective seed, and
        based on the oil mass, compute an oil content value for each respective seed within a time period dictated by the selected constant rate of speed of the conveyor belt.

2. The system of claim 1 further comprising a microwave resonance cavity structured and operable to receive and have pass therethrough, without pause, each seed after each respective seed has been conveyed through the NMR assembly and to obtain total seed mass data for each respective seed.

3. The system of claim 2, further comprising a diverter assembly structured and operable to receive the seeds from the microwave resonance cavity and, via commands from the central control system, separate the seeds based on the computed oil/moisture content of each respective seed.

4. The system of claim 2, wherein the NMR assembly comprises:
    an NMR rexlameter structured and operable to exert a magnetic force on each seed passing through the NMR assembly; and
    a radio frequency (RF) probe structured and operable to generate a plurality of pulses and receive an echo from each pulse from which the at least one of oil and moisture mass data is generated.

5. The system of claim 4, wherein the number of pulses generated each millisecond is such that noise generated by each pulse cancels the noise of subsequent pulses, thereby increasing the signal-to-noise ratio of NMR measurement during determination of the at least one of oil and moisture mass data.

6. The system of claim 5, wherein the number of pulses generated each millisecond is approximately five pulses per millisecond.

7. The system of claim 1, wherein each seed cup comprises a reservoir into which each respective seed is deposited by the seed feeder assembly and a plurality of serrations through a body of seed cup, the reservoir and serrations structured and operable to center and reduce vibration of each seed within the respective seed cup and retain each seed in a stable orientation within the respective seed cup as each seed is conveyed through the NMR assembly.

8. The system of claim 1, wherein the selected rate of speed is approximately one meter per second.

9. The system of claim 1 further comprising a stray seed removal assembly structured and operable to remove stray seeds that are not retained within a seed cup from the conveyor belt.

10. A high throughput seed sorting system, said system comprising:
    a conveyor assembly including a conveyor belt having a plurality of seed cups attached thereto, the conveyor assembly structured and operable to continuously move the conveyor belt at a selected constant rate of speed during operation of the system;
    a seed feeder assembly structured and operable to singulate seeds from a plurality of seeds and deposit each singulated seed into a respective one of the seed cups as the conveyor belt continuously moves at the selected constant rate of speed;
    a nuclear magnetic resonance (NMR) assembly having the conveyor belt operably extending therethrough, the NMR assembly structured and operable to generate at least one of oil and moisture mass data for each seed as each seed moves through the NMR assembly at the selected constant rate of speed;
    a computer based central control system structured and operable to:
        receive the at least one of oil and moisture mass data from the NMR assembly for each seed, and
        execute oil/moisture content software to store the at least one of oil and moisture mass data for each seed and associate the at least one of oil and moisture mass data received for each seed with the respective seed; and
    a diverter assembly structured and operable to receive the seeds and, via commands from the central control system, separate the seeds based on the at least one of oil and moisture mass data of each respective seed.

11. A method for high throughput seed sorting, said method comprising:
- continuously moving a conveyor belt at a selected constant rate of speed, the conveyor belt included in a conveyor assembly of a high throughput seed sorting system and having a plurality of seed cups attached thereto;
- singulating seeds from a plurality of seeds and depositing each singulated seed into a respective one of the seed cups as the conveyor belt continuously moves at the selected constant rate of speed;
- generating at least one of oil and moisture mass data for each seed as each seed moves through a nuclear magnetic resonance (NMR) assembly at the selected constant rate of speed; and
- separating the seeds into at least two subsets based on the at least one of oil and moisture mass data of each respective seed.

* * * * *